(12) United States Patent
Oldenburg et al.

(10) Patent No.: US 9,675,953 B2
(45) Date of Patent: Jun. 13, 2017

(54) ENCAPSULATED PARTICLES

(71) Applicant: nanoComposix, Inc., San Diego, CA (US)

(72) Inventors: Steven J. Oldenburg, San Diego, CA (US); Richard K. Baldwin, San Diego, CA (US)

(73) Assignee: nanoComposix, Inc., San Diego, CA (US)

( * ) Notice: Subject to any disclaimer, the term of this patent is extended or adjusted under 35 U.S.C. 154(b) by 0 days.

(21) Appl. No.: 15/027,426

(22) PCT Filed: Oct. 9, 2014

(86) PCT No.: PCT/US2014/059902
§ 371 (c)(1),
(2) Date: Apr. 5, 2016

(87) PCT Pub. No.: WO2015/054493
PCT Pub. Date: Apr. 16, 2015

(65) Prior Publication Data
US 2016/0250612 A1 Sep. 1, 2016

Related U.S. Application Data

(60) Provisional application No. 61/961,264, filed on Oct. 9, 2013, provisional application No. 61/961,268, filed
(Continued)

(51) Int. Cl.
*B01J 13/20* (2006.01)
*C01B 33/113* (2006.01)
(Continued)

(52) U.S. Cl.
CPC ............ *B01J 13/20* (2013.01); *A61K 9/5115* (2013.01); *B01J 13/18* (2013.01); *B22F 1/0018* (2013.01);
(Continued)

(58) Field of Classification Search
None
See application file for complete search history.

(56) References Cited

U.S. PATENT DOCUMENTS

| 7,223,454 | B1 | 5/2007 | Bringley et al. |
| 7,229,690 | B2 * | 6/2007 | Chan ........................ B01J 13/02 428/403 |

(Continued)

FOREIGN PATENT DOCUMENTS

| JP | 2009-507592 | 2/2009 |
| WO | WO 2007-031345 | 3/2007 |

OTHER PUBLICATIONS

International Search Report dated Jan. 29, 2015 in International Patent Application No. PCT/US2014/059902.

*Primary Examiner* — Alexandre Ferre
(74) *Attorney, Agent, or Firm* — Knobbe, Martens, Olson & Bear LLP

(57) ABSTRACT

The disclosed technology relates generally to material systems which include a plurality of particles and methods of making the same. The particles have a core and a shell which encapsulates the core and has at least one atomic element not included in the core. The cores of the particles have a median maximum dimension that is less than 10 microns and a median of at least one axial dimension that is between 10 nm and 500 nm. The shells of the particles have a median thickness that is less than 100 nm, a silicon concentration that is between 10% and 50% on the basis of the weight of the shells, and an aluminum concentration that is between 0.01% and 5% on the basis of the weight of the shells.

49 Claims, 14 Drawing Sheets

Related U.S. Application Data on Oct. 9, 2013, provisional application No. 61/966,815, filed on Mar. 4, 2014.

(51) Int. Cl.

| | |
|---|---|
| B22F 9/16 | (2006.01) |
| A61K 9/51 | (2006.01) |
| C01B 33/18 | (2006.01) |
| B01J 13/18 | (2006.01) |
| C09B 67/02 | (2006.01) |
| C01B 33/26 | (2006.01) |
| B22F 1/00 | (2006.01) |
| B22F 1/02 | (2006.01) |
| G01N 33/543 | (2006.01) |
| C09B 67/08 | (2006.01) |

(52) U.S. Cl.
CPC .......... *B22F 1/0025* (2013.01); *B22F 1/0062* (2013.01); *B22F 1/02* (2013.01); *B22F 9/16* (2013.01); *C01B 33/113* (2013.01); *C01B 33/18* (2013.01); *C01B 33/26* (2013.01); *C09B 67/0007* (2013.01); *C09B 67/0097* (2013.01); *G01N 33/54346* (2013.01); *B22F 2001/0033* (2013.01); *B22F 2001/0037* (2013.01); *B22F 2009/165* (2013.01); *B22F 2301/255* (2013.01); *B22F 2302/45* (2013.01)

(56) References Cited

U.S. PATENT DOCUMENTS

| | | | |
|---|---|---|---|
| 7,563,457 B2 * | 7/2009 | Cha | A61K 47/48861 424/489 |
| 2004/0067503 A1 * | 4/2004 | Tan | B82Y 15/00 435/6.1 |
| 2009/0114797 A1 | 5/2009 | Beals et al. | |
| 2011/0190561 A1 | 8/2011 | Bulut et al. | |
| 2012/0211074 A1 | 8/2012 | Sager et al. | |
| 2012/0295790 A1 * | 11/2012 | Yan | A01N 25/28 504/273 |
| 2013/0228716 A1 * | 9/2013 | Suetsuna | B22F 1/02 252/62.55 |

* cited by examiner

ENCAPSULATED PARTICLES

CROSS-REFERENCE TO RELATED APPLICATIONS

The present application is the U.S. National Phase under 35 U.S.C. §371 of International PCT application number PCT/US 2014/059902, filed Oct. 9, 2014, which claims priority to U.S. Provisional Application No. 61/961,264, filed Oct. 9, 2013, U.S. Provisional Application No. 61/961,268, filed Oct. 9, 2013, and U.S. Provisional Application No. 61/966,815, filed Mar. 4, 2014. The contents of each are incorporated herein by reference in their entireties.

BACKGROUND

Field

The disclosed technology generally relates to material systems which include a plurality of particles, and more particularly to material systems that include composite particles having a core and one or more shells that enclose the core.

Description of the Related Art

Various materials, e.g., metals and metal oxides, can be produced in the form of particles, which can have enhanced properties compared to their bulk counterparts because of, for example, their size and/or surface/volume ratio. For some applications, it may be desirable to at least temporarily prevent the particles from being exposed to external environments. One to way to limit the exposure of the particles to the external environments is to coat the particles with a protective material such as, for example, silicon oxide. Silicon oxide coatings can be formed using a variety of techniques. However, silicon oxide, while effective against some environments, can be ineffective against some other environments. For example, for many biological applications, particles coated with silicon oxide may be subjected to solution environments, e.g., aqueous solutions, in which silicon oxide has an unacceptable dissolution rate (e.g., nanometers within days, depending on the application). Premature dissolution of the protective coating and the resulting exposure of the core particle surface species can be undesirable for many biological applications, since surface-bound targeting molecules can be prematurely released from the particle surface.

To improve the stability of silicon oxide coatings of particles against dissolution in certain environments, e.g., water, a number of techniques can be employed, including, for example, heating in solution, calcining and maintaining the silica in a non-aqueous solution. Heating in solution only partially reduces the solubility of silicon oxide. Calcining, which refers to a process in which silicon oxide is heated to high temperatures (e.g. >200° C.), is effective at condensing Si—OH bonds into Si—O—Si linkages, thus increasing the stability. However, the high temperatures can increase particle agglomeration, making it difficult to redisperse the particles in uniform suspension. The calcination step can also affect other chemical entities within or on the surface of the particles such as the free amines, thiols or carboxylic acids which are utilized for attaching targeting molecules to the surface of the silica particles. While retaining the silica in an organic solvent can prevent dissolution of silicon oxide coating, such methods may not be relevant for many biological applications that require them to be maintained in an aqueous solutions. Thus, there is a need for protective coating of particles that offer greater stability against dissolution in aqueous environments.

SUMMARY

In a first aspect, a material composition comprises a plurality of particles, wherein each particle comprises a core and a shell encapsulating the core, the shell comprising at least one atomic element not included in the core. The cores have a median maximum dimension that is less than 10 microns and a median of at least one axial dimension that is in the range of 10 nm to 500 nm. The shells have a median thickness that is less than 100 nm, a silicon concentration that is in the range of 10% to 50% on the basis of the weight of the shells, and an aluminum concentration that is in the range of 0.01% to 5% on the basis of the weight of the shells.

In an embodiment, the shells comprise a three-dimensional network of interconnected molecular units, comprising: a first plurality of molecular units having a chemical formula $SiO_x(OH)_y$, wherein $x+y \leq 4$ and x is $\geq 1$; a second plurality of molecular units having a chemical formula $SiO_a(OH)_b R_c$, wherein $a+b+c \leq 4$, a is $\geq 1$ and R is a chemical group having a carbon atom that is directly bonded to a silicon atom; and a third plurality of molecular units having a chemical formula $AlO_m(OH)_n$, wherein $m+n \leq 6$ and m is $\geq 1$. At least one oxygen atom in each of the first, second and third molecular units is covalently bonded to two silicon atoms, to a silicon atom and an aluminum atom, or to two aluminum atoms.

In an embodiment, at least 95% of the shells, on the basis of atomic percentage, comprise silicon, carbon, oxygen, hydrogen, and aluminum. In an embodiment, the at least 98% of the shells further comprise nitrogen and sulfur.

In an embodiment, the material composition further comprises a liquid in which the particles are immersed, the liquid comprising at least 50% water by volume.

In an embodiment, the silicon and aluminum concentrations are selected such that the median thickness of the shells does not change by more than 10% when measured 24 hours after immersing in the solution, compared to the median thickness prior to immersing.

In an embodiment, R comprises a chemical group selected from the group consisting of an amine, a thiol, a carboxylic acid, an azide, an aldehyde, an epoxide and combinations thereof.

In an embodiment, the core has a shape selected from the group consisting of a sphere, a spheroid, an ellipsoid, a pyramid, a prism, a cube, a plate, a disc, a rod and a hollow sphere.

In an embodiment, the core comprises an element selected from the group consisting of gold, silver, platinum, palladium, copper, aluminum, nickel, and iron.

In an embodiment, the core comprises an inorganic oxide selected from the group consisting of $SiO_2$, $TiO_2$, $Fe_2O_3$, $Fe_3O_4$, CuO, $Cu_2O$, ZnO, $Y_2O_3$, $ZrO_2$, $Nb_2O_5$, $MoO_3$, $In_2O_3$, $SnO_2$, $Sb_2O_5$, $Ta_2O_5$, $WO_3$, PbO and $Bi_2O_3$, and combinations thereof.

In an embodiment, at least one of the core and the shell comprises a plurality of nanoparticles incorporated therein, wherein the nanoparticles have a median maximum dimension that is less than 100 nm.

In an embodiment, each particle further comprises a plurality of nanoparticles formed at an interface between the core and the shell, wherein the nanoparticles are in contact with the core but formed outside of the core.

In an embodiment, each particle further comprises a plurality of nanoparticles formed at surfaces of the shells.

In an embodiment, the nanoparticles are selected from the group consisting of quantum dot nanoparticles, magnetic nanoparticles, up-converting nanoparticles, down-converting nanoparticles, gold nanoparticles, silver nanoparticles, aluminum nanoparticles, copper nanoparticles and combinations thereof.

In an embodiment, the nanoparticles are quantum dot nanoparticles comprising a semiconductor material selected from the group consisting of Si, Ge, CdS, CdSe, CdTe, ZnS, ZnSe, ZnTe, GaAs, GaP, GaAs, GaSb, HgS, HgSe, HgTe, InAs, InP, InSb, AlAs, AlP, and AlSb, wherein the quantum dot nanoparticles emit light having a peak wavelength at least 10 nanometers shorter than an emission wavelength of a bulk semiconductor material having the same composition as the semiconductor material.

In an embodiment, the nanoparticles have a core-shell structure, wherein the nanoparticles have a nanoparticle core comprising the semiconductor material and a nanoparticle shell comprising a material different from the nanoparticle core material.

In an embodiment, the nanoparticles are magnetic nanoparticles selected from the group consisting of iron, cobalt, nickel, gadolinium, dysprosium iron and their associated oxides, wherein the nanoparticles have a magnetic moment that is at least 1 emu/g.

In an embodiment, at least 90% of the nanoparticles have a median edge-to-edge spacing of at least 2 nm.

In an embodiment, at least 90% of the nanoparticles have a median edge-to-edge spacing of less than 2 nm.

In an embodiment, each particle further comprises an intermediate shell interposed between the core and the shell, wherein the intermediate shell comprises a material different than the core and the shell.

In an embodiment, one or both of the shell and the intermediate shell comprises a metal or an inorganic metal oxide.

In an embodiment, at least one of the core, the intermediate shell and the shell comprises a plurality of nanoparticles incorporated therein, wherein the nanoparticles have a median maximum dimension that is less than 100 nm.

In an embodiment, each particle further comprises a plurality of nanoparticles formed at one or both of an interface between the core and the intermediate shell and an interface between the intermediate shell and the shell.

In an embodiment, the material composition further comprises a bifunctional linker molecule or a biomolecule attached to a surface of each particle.

In an embodiment, the material composition further comprises a molecule selected from the group consisting of a protein, antibody, DNA, RNA and combinations thereof, wherein the molecule is bonded to a particle surface.

In an embodiment, the particles further comprise a molecule selected from the group consisting of a protein, antibody, DNA, RNA and a combination thereof, wherein the molecule is encapsulated within the core and/or the shell.

In an embodiment, the material composition further comprises a molecule selected from the group consisting of a sugar, a small organic molecule, a polymer molecule and a combination thereof, wherein the molecule is attached to a particle surface.

In an embodiment, a surface of each particle is functionalized with a functional group selected from the group consisting of a thiol group, a carboxyl group, an aldehyde group, a carboxylic acid group, hydrazide group, an amine group and combinations thereof.

In an embodiment, the material composition further comprises a molecule selected from the group consisting of a biotin, a streptavidin, a folate or a combination thereof, wherein the molecule is attached to a particle surface.

In an embodiment, at least one of the core or the shell includes a light-emitting center incorporated therein, wherein the light-emitting center is selected from the group consisting of fluorophore, dye, luminophore, a chemiluminescent species and phosphor.

In an embodiment, the material composition further comprises one or more light-emitting centers attached to a particle surface.

In an embodiment, the material composition further comprises a plurality of quantum-dot nanoparticles attached to a particle surface, wherein the quantum-dot nanoparticles are functionalized with streptavidin.

In an embodiment, the core comprises a silicon oxide having a plurality of magnetic nanoparticles incorporated therein, and wherein the shell comprises a DNA molecule, an RNA molecule and/or a peptide molecule.

In a second aspect, a method of preparing a material composition comprises providing a plurality of particle cores. The method additionally comprises encapsulating the particle cores with shells comprising at least one atomic element not included in the cores. The method further comprises incorporating aluminum into the shells by exposing the shells to an aluminum-containing material to thereby provide a plurality of particles. The particle cores have a median maximum dimension that is less than 10 microns, and a median of at least one axial dimension that is in the range of 10 nm to 500 nm. The shells have a median thickness that is less than 100 nm, a silicon concentration that is in the range of 10% to 50% on the basis of the weight of the shells, and an aluminum concentration that is in the range of 0.01% to 5% on the basis of the weight of the shells.

In an embodiment, the method further comprises immersing the particles in a liquid that comprises at least 50% water by volume.

In an embodiment, the liquid which dissolves up to 2 nm thickness of silicon dioxide shells that do not have an aluminum concentration exceeding 0.01% at room temperature.

In an embodiment, the method further comprises storing the immersed particles in the liquid for at least 24 hours, wherein the median thickness of the shells does not change by more than 10% when measured 24 hours after immersing in the liquid, compared to the median thickness prior to immersing.

In an embodiment, encapsulating the particle cores includes forming a three-dimensional network of interconnected molecular units surrounding the particle cores, wherein the three-dimensional network comprises: a first plurality of molecular units having a chemical formula $SiO_x(OH)_y$, wherein $x+y \leq 4$ and $x$ is $\geq 1$, and a second plurality of molecular units having a chemical formula $SiO_a(OH)_b R_c$, wherein $a+b+c \leq 4$, $a$ is $\geq 1$ and R is a chemical group having a carbon atom that is directly bonded to a silicon atom. Incorporating aluminum into the shells comprises incorporating aluminum into the three-dimensional network such that the three dimensional network is modified to include a third plurality of molecular units having a chemical formula $AlO_m(OH)_n$, wherein $m+n \leq 6$ and $m$ is $\geq 1$. At least one oxygen atom in each of the first, second and third molecular units is covalently bonded to two silicon atoms, to a silicon atom and an aluminum atom, or to two aluminum atoms.

In an embodiment, encapsulating the cores comprises forming a silicon oxide via a condensation reaction in a solution containing at least one silane having a chemical formula given by $X_nSiY_{(4-n)}$, wherein 0<n<4, and wherein one or both of X and Y is selected from the group consisting of OEt, OMe, Cl, Br, I, H, alkyl, fluoroalkyl, perfluoroalkyl, alkoxide, aryl, alkyl amine, alkyl thiol and combinations thereof.

In an embodiment, the at least one silane is selected from the group consisting of aminopropyltriethoxy silane, aminopropyltrimethoxy silane, mercaptopropyltriethoxysilane, mercaptopropylmethoxysilane, tetramethoxy silane, tetraethoxy silane, and combinations thereof.

In an embodiment, incorporating aluminum comprises exposing the shells to a solution having an aluminum salt dissolved therein. In an embodiment, the aluminum salt is aluminum chloride.

In an embodiment, the concentration of the aluminum salt in the solution is in the range of 0.1 to 100 mM.

In an embodiment, incorporating aluminum is performed during encapsulating the cores by adding the aluminum salt to the solution while the particle cores are being encapsulated with the shells.

In an embodiment, incorporating aluminum is performed after encapsulating the cores by transferring cores encapsulated with the shells to an aqueous solvent before the aluminum salt is dissolved therein.

In an embodiment, the provided plurality of particle cores comprises an element selected from the group consisting of silver, gold, aluminum and copper.

In an embodiment, the provided plurality of particle cores comprise an inorganic oxide selected from the group consisting of $SiO_2$, $TiO_2$, $Fe_2O_3$, $Fe_3O_4$, CuO, $Cu_2O$, ZnO, $Y_2O_3$, $ZrO_2$, $Nb_2O_5$, $MoO_3$, $In_2O_3$, $SnO_2$, $Sb_2O_5$, $Ta_2O_5$, $WO_3$, PbO and $Bi_2O_3$, and combination thereof.

In an embodiment, the method further comprises incorporating a plurality of nanoparticles into at least one of the cores and the shells, wherein the nanoparticles have a median maximum dimension that is less than 100 nm.

In an embodiment, the method further comprises forming a plurality of nanoparticles at one or both of interfaces between the cores and the shells and surfaces of the particles.

DETAILED DESCRIPTION OF THE PREFERRED EMBODIMENTS

Figure 1A:
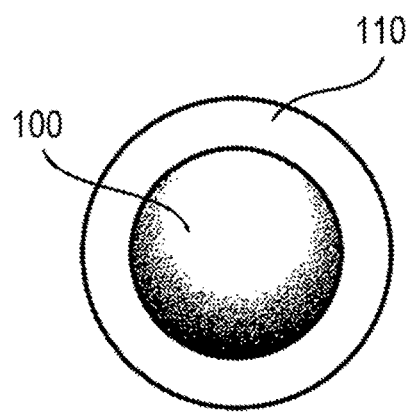
FIG. 1A is a schematic cross-sectional view of a particle having a core and a shell, according to some embodiments.

Various materials, e.g., metals and metal oxides, can be produced in the form of particles, which can have enhanced properties compared to their bulk counterparts because of, for example, their size and/or surface/volume ratio. For some applications, it may be desirable to at least temporarily prevent the particles from being exposed to external environments. One to way to limit the exposure of the particles to the external environments is to coat the particles with a protective material such as, for example, silicon oxide.

As described herein, silicon oxide refers to amorphous oxide of silicon that may or may not be stoichiometric. A stoichiometric silicon oxide ($SiO_2$) is understood to comprise a three-dimensional network of tetrahedrally coordinated silicon atoms (i.e., coordinated by four oxygen atoms), while a sub-stoichiometric silicon oxide ($SiO_x$) is understood to comprise a three-dimensional network where silicon atoms are coordinated by less than four oxygen atoms. Thus, a silicon oxide thus refers to an oxide of silicon that can be represented by a chemical formula $SiO_x$, where x is 2 or less. Furthermore, it will be understood that a silicon oxide can have some other atoms incorporated therein, such as, for example, hydrogen (H), carbon (C), nitrogen (N), and sulfur (S), and aluminum (Al), among other impurities. When aluminum is incorporated into silicon oxide, at least some aluminum atoms can replace the silicon atoms of silicon oxide. As used herein, such silicon oxide having aluminum atoms incorporated therein is referred to as aluminum silicate, aluminum-containing silicon oxide, or aluminum-incorporated silicon oxide.

Silicon oxide coatings can be formed using a variety of techniques. For example, metal and metal oxide particles can be coated with silicon oxide via sol gel methods, using a wide variety of different silanes that can be condensed onto the surface of the particles without aggregating. Advantageously, forming silicon oxides via condensation using various silane precursors allows different chemical functionalities to be integrated into the silicon oxide shell. For example, coupling of recognition ligands such as antibodies or DNA to the surface of silicon oxide nanoparticles allows the particles to target specific cells or to identify antigens. Biofunctionalized silicon oxide nanoparticles have been utilized extensively in clinical diagnostics and as therapeutics.

However, silicon oxide coatings, while effective against some environments, can be ineffective against some environments, e.g., biological environments. For example, for many biological applications, particles coated with silicon oxide may be subjected to solution environments, e.g., aqueous solutions, in which silicon oxide has an unacceptable dissolution rate (e.g., nanometers within days). Premature dissolution of the protective coating and the resulting exposure of the core particle surface species can be undesirable for many biological applications, since surface-bound targeting molecules can be prematurely released from the particle surface.

The inventors have found that incorporating aluminum atoms into the molecular network of the silicon oxide coating can dramatically increase stability in aqueous solutions, e.g., water, compared to silicon oxide coatings without aluminum. The increased stability is important for ensuring that the physical and optical properties of the shell are maintained in aqueous and high humidity environments. The stable shell surface allows for long term encapsulation of fluorescent, magnetic, and/or optically responsive molecules and nanoparticles. Biological targeting agents remain bound to the surface of aluminum stabilized silicon oxide shells for extended periods of time which increases the shelf life of aluminum silicate-shelled probes. The core-shell particles may be included in compositions that may be used for antimicrobial formulations, dermatology treatments, taggants, tracers, diagnostic assays, markers, inks, labels and coatings, of which at least one of the shells is aluminum silicate. The aluminum silicate shell has increased stability in water compared to silicon oxide shells without aluminum. The increased stability is important for ensuring that the physical and optical properties of the shell are maintained in aqueous and high humidity environments. The stable shell surface allows for long term encapsulation of fluorescent, magnetic, and/or optically responsive molecules and nanoparticles. Biological targeting agents remain bound to the surface of aluminum stabilized silicon oxide shells for extended periods of time which increases the shelf life of aluminum silicate-shelled probes. The core-shell particles may be included in compositions that may be used for antimicrobial formulations, dermatology treatments, taggants, tracers, diagnostic assays, markers, inks, labels and coatings.

Particles Having a Core-Shell Structure

Figure 1B:
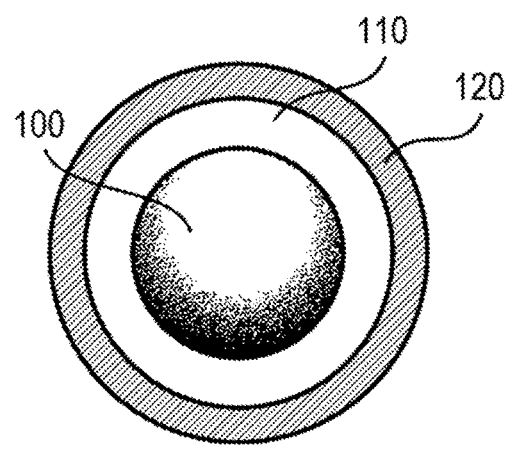
FIG. 1B is a schematic cross-sectional view of a particle having a core and a plurality of shells, according to some embodiments.

FIGS. 1A and 1B are schematic cross-sectional views of particles of material compositions according to some embodiments. According to one embodiment, a material composition comprises a plurality of particles wherein each particle comprises a core 100 and one or more shells 110 and/or 120. As described herein, a core of a particle having a core-shell structure refers to an inner portion that does not surround another portion of the particle. However, as described infra, the core can enclose a void. As described herein, a shell of a particle having a core-shell structure refers to an outer portion that surrounds another portion, which can be a core or another shell surrounding the core.

The one or more shells 110 and/or 120 comprise at least one atomic element not included in the core. The cores are characterized by lengths along the three principle axes wherein the axial length of the core's longest principle axes has a median average dimension less than 50 microns, 10 microns, 5 microns, 2 microns, 1 micron or 500 nm. In an embodiment, the core has dimensions between 10 nm and 10 microns, 10 nm and 50 microns, 10 nm and 100 microns, 20 nm and 50 microns, 20 nm and 10 microns, 50 nm and 10 microns, 50 nm and 2 microns, or 50 nm and 1000 nm. In an embodiment, the median of at least one of the axial dimensions of the core is less than 1 micron, 500 nm, 300 nm, 200 nm, 100 nm, 50 nm, 20 nm or 10 nm. In an embodiment, the median of at least one of the axial dimensions is between 10 nm and 1000 nm, 10 nm and 500 nm, 20 nm and 500 nm, 50 nm and 500 nm, 20 nm and 300 nm, 20 nm and 200 nm, or 50 nm and 200 nm. In an embodiment, the core is a nanoplate that has a thickness less than 50 nm, 40 nm, 30 nm or 20 nm and a diameter that is greater than 10, 20, 30, 40, 50, 80, or 100 nm.

In an embodiment, a plurality of core particles are encapsulated with one or more shells comprising a material that has at least one atomic element not included in the core. In an embodiment, the shell has a thickness less than 300 nm, 200 nm, 100 nm, 75 nm, 50 nm, 25 nm or 10 nm. In an embodiment, the shell has a thickness between 0.1 nm and 100 nm, 1 nm and 10 nm, 1 nm and 100 nm, 1 nm and 300 nm, 2 nm and 100 nm, 5 nm and 100 nm or 10 nm and 100 nm.

In the illustrated embodiments of FIGS. 1A and 1B, the cores are encapsulated with one or more shells of a material which comprises an aluminum silicate. FIG. 1A illustrates a particle having a core 100 encapsulated with a single aluminum silicate shell 110. FIG. 1B is a schematic of a core 100 encapsulated with an intermediate shell 110 that is further encapsulated with an aluminum silicate shell 120. An intermediate shell can include one or more shells that are radially interposed between the core 100 and the outer shell 120.

Figure 2:
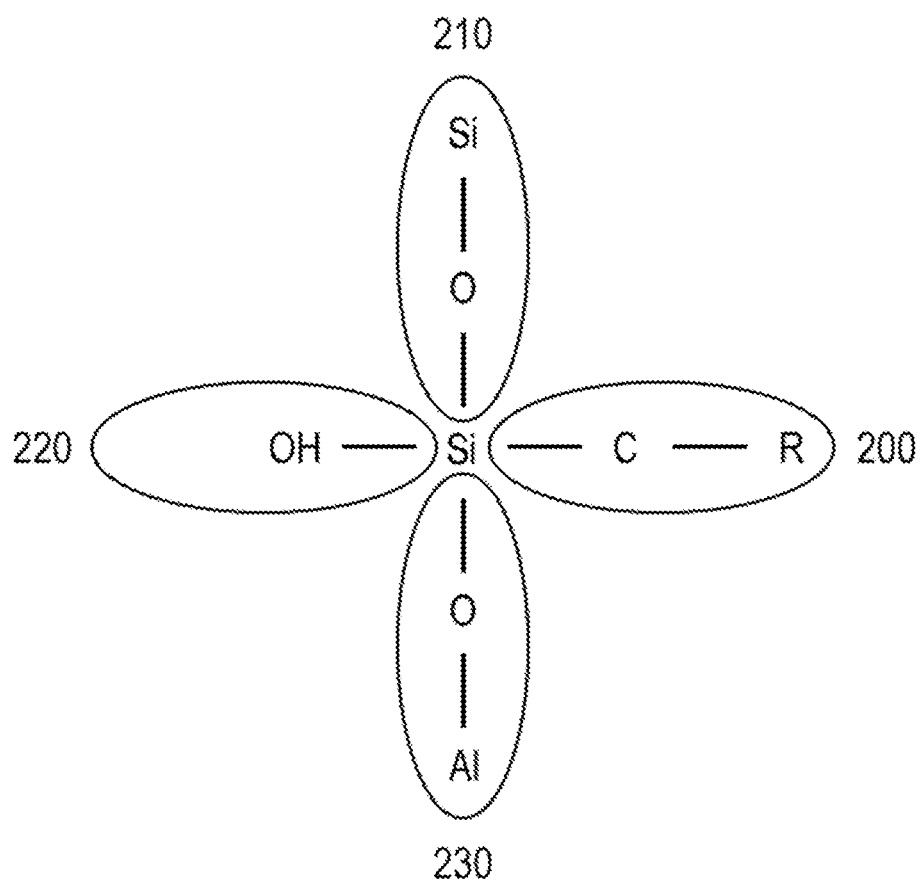
FIG. 2 is a schematic representation of different functional groups that can be linked to a silicon atom of a particle shell, according to embodiments.

FIG. 2 is a schematic representation of different functional groups that can be linked to a silicon atom of a particle shell, according to embodiments. A silicate shell includes a three dimensional network of silicon atoms where a silicon atom is connected by at least one oxygen atom to another silicon atom. An aluminum silicate shell is a three dimensional network of silicon and aluminum atoms where a silicon atom or an aluminum atom is connected by at least one oxygen atom to another silicon or aluminum atom. Each silicon atom can have up to four bonds. Bonds can connect to another silicon or aluminum atom through an oxygen bridge, bonds can connect to OH— groups, and bonds can connect to organic groups connected to the silicon via a carbon.

FIG. 2 schematically shows 4 types of functional groups, also referred to herein as molecular units or moieties that can bind to a silicon atom in the three dimensional network of an aluminum silicate shell according to embodiments. While first to fourth functional groups 200, 210, 220 and 230 are illustrated as being bound to a common silicon atom, such representation is for illustrative purposes only, and actual aluminum silicate shell can have anywhere from zero to four of any one of the four functional groups. The first functional group 200 is a representation of the binding of a silicon atom to a carbon atom that is linked to an organic molecule, R. The second functional group 210 is a representation of the binding of a silicon atom to another silicon atom through an oxygen atom. The third functional group 220 is a representation of the binding of a silicon atom to a hydroxyl group and. The fourth functional group 230 is a representation of the binding of a silicon atom to an aluminum atom via an oxygen atom. In an embodiment, the average number of 210 and 230 linkages for all of the silicon atoms in the aluminum silicate shell is at least 1. In an embodiment, the average number of hydroxyl groups connected to the silicon atoms in the aluminum silicate is less than 2, 1, 0.5, 0.3, 0.2, 0.1, 0.05, 0.01 or 0.001 per silicon atom. In another embodiment, the percentage of the moieties that are bound to silicon atoms that consist of hydroxyl groups is less than 95%, 90%, 80%, 70%, 60%, 50%, or 25%.

In an embodiment, the aluminum silicate shell comprises organically modified silicate moieties that have different R groups. Each silicon atom can be linked to 0, 1, 2, or 3 R groups. R groups can consist of all carbon or be a mixture of carbon and other atoms such as hydrogen, nitrogen, sulfur and/or oxygen. In one embodiment, the R group comprises a molecule group chosen from a group consisting of an amine, a thiol, a carboxylic acid, an azide, an aldehyde, an epoxide and combinations thereof.

In an embodiment, the silicon moieties in the aluminum silicate shell arise from the hydrolysis of mixtures containing one or more silicon containing species of the form $Si(OR1)_d R2_e$ where $d \geq 1$, $e \leq 3$, $d+e=4$ and e can be zero and OR1 is an alkoxide and R2 is an alkyl chain with a direct C—Si bond that may or may not have other atoms other than carbon or hydrogen present. Specific examples of silicate precursors of this type include but are not limited to tetraalkoxysilane such as tetraethoxysilane or tetramethoxysilane; and a trialkoxysilane compound such as methyltrimethoxysilane, methyltriethoxysilane and phenyltriethoxysilane, mercaptopropyltriethoxysilane and aminopropyltriethoxysilane.

In another embodiment the R2 groups contain one or more alkyl, alkoxy, organochloro, oxalkyl, ethenyl, alcohols, ketones, epoxides, amines, thiols, carboxylic acids, polyethylene glycols, azides or aldehydes. Such silicon containing alkoxide species are commercially available from companies such as Gelest (Morrisville, Pa.). The alkoxide species hydrolyze to form unstable SiOH groups, some portion of which subsequently condense to give rise to Si—O—Si bonds. If the particular silane that condensed has an R2 group present then that R2 group will not be hydrolyzed and will be incorporated in the silicon oxide shell, adding additional chemical functionality. This functionality may include a potential site for additional chemical elaboration.

In one embodiment, the precursor silane may contain an amine. Although no particular limitation is placed on the molecules that have an amino group and at least one type of silyl group substituted by a hydrolyzable substituent group, such molecules include various types of compounds referred to as silane coupling agents. Specific examples include 3-aminopropylmethyl dimethoxysilane, 3-aminopropyltriethoxysilane, 3-aminopropyltrimethoxysilane, aminopropyltrimethoxy silane and aminopropyl triethoxysilane. In a preferred embodiment the precursors from which the silicon oxide of the aluminum silicate shell arise comprise tetraethylorthosilicate, aminopropyltrimethoxy silane, and aminopropyltriethoxy silane.

The type and number of organically modified silicates that are incorporated into the aluminum silicate shell affect the mass percentage of Si in the aluminum silicate shell. In an embodiment, the mass percentage of Si is at least 5%, 10%, 20%, 30%, 40%, or 50%. In an embodiment, the mass percentage of Si is between 3% and 50%, 3% and 40%, 3% and 30%, 3% and 20%, 5% and 50%, 5% and 40%, 5% and 30%, 10% and 50%, 10% and 40%, 10% and 30%, 10% and 25%, or 20% and 50%. In an embodiment, the mass percentage of aluminum is at least 0.01%, 0.02%, 0.05%, 0.1%, 0.2%, 0.5%, 1.0%, 2.0%, 5.0%, 10% or 20%. In an embodiment, the mass percentage of aluminum is in the range of 0.01% to 20%, 0.01% to 10%, 0.01% to 5%, 0.1% to 20%, 0.1% to 10%, 0.1% to 5%, 0.2% to 5%, 0.1% to 3%, or 0.1% to 2%. In an embodiment, the ratio of Al to Si is at least 1:2, 1:5, 1:10, 1:20, 1:50, 1:100, 1:300, 1:500, 1:1000, or 1:5000. In an embodiment, the ratio of Al to Si is in the range of 1:2 to 1:5000, 1:5 to 1:5000, 1:10 to 1:5000, 1:20 to 1:5000, 1:2 to 1:1000, 1:5 to 1:1000, 1:10 to 1:1000, 1:20 to 1:1000, 1:5 to 1:300, 1:10 to 1:300, 1:20 to 1:300, 1:5 to 1:100, 1:10 to 1:100, 1:20 to 1:100, 1:5 to 1:50, or 1:10 to 1:50. In an embodiment, at least 50%, 60%, 70%, 80%, 90%, 95%, 97%, 98%, 99%, 99.5% or 99.9% of the aluminum silicate shell on the basis of atomic percentage comprises silicon, carbon, oxygen, hydrogen, and aluminum. In an embodiment, at least 50%, 60%, 70%, 80%, 90%, 95%, 97%, 98% or 99%, 99.5% or 99.9% of the aluminum silicate shell on the basis of atomic percentage comprises silicon, carbon, oxygen, hydrogen, aluminum, nitrogen and sulfur.

In various embodiments, the aluminum silicate shell comprises a plurality of molecular units of silicon oxide, organically modified silicon oxide and alumina. A first plurality of molecular units are silicon oxide molecular units that have average molecular ratios of $SiO_x(OH)_y$, wherein x+y≤4, x is ≥1. A second plurality of molecular units are organically modified silicon oxide molecular units that have average molecular ratios of $SiO_a(OH)_b R_c$ wherein a+b+c≤4, a is ≥1 and R includes a molecule having a carbon atom that is directly bonded to a silicon atom. A third plurality of molecular units are alumina molecular units that have average molecular ratios of $AlO_m(OH)_n$ wherein m+n≤6, m is ≥1. The three types of molecular units are bonded together with oxygen atom bridges into a three dimensional structure, where at least one of the single oxygens in each of these formulas ($O_x$, $O_a$, and $O_m$) is an oxygen bridging between two silicon atoms, a silicon and an aluminum atom, or two aluminum atoms. The numbers a, b, c, m, n, x and y can be whole or fractional numbers that represent the average ratio for each of the silica, organically modified silica, and alumina components of the matrix. In an embodiment, functionalized silicon oxide and alumina species exist in the shell in a mole ratio such that silicon oxide mole ratio is greater than organically modified silicon oxide, which in turn is greater than the mole ratio of alumina. In some embodiments the ratio of silicon oxide containing species to alumina containing species is at least greater than 2, greater than 5, greater than 10, greater than 20, greater than 100 or greater than 1000. In some embodiments the ratio of silicon oxide to organically modified silicon oxide is greater than 0.1, 0.5, 1.0, 2.0, 5.0, 10.0, 20, 100, or 200. In some embodiments, the shell comprises only organically modified silicon oxide and alumina.

Characterization of the composite particles relies on techniques known to those skilled in the art. These techniques include transmission electron microscopy (TEM), scanning electron microscopy (SEM), atomic force microscopy (AFM), inductively coupled plasma mass spectrometry (ICP-MS), infrared spectroscopy elemental analysis and x-ray powder diffraction. To determine the particle morphology, TEM, SEM and AFM can be utilized to determine the average axial dimensions of the particles. For some embodiments, TEM can be used to determine the relative dimensions of the core and shell. Different materials can have different electron densities which are imaged as different levels of contrast in TEM micrographs. In these embodiments, this allows for independent measurement of the core size and shape as well as the shell size, shape and thickness.

To characterize the elemental composition of the core shell particles, ICP-MS or other elemental analysis can be employed. By utilizing the porosity of the shell and the differential solubilities of the various components of the particle it can be possible to dissolve out the component of interest and independently determine its elemental composition. Silicon oxide-based materials can be dissolved in HF solutions while most other materials are inert to HF. In addition, silicon oxide and aluminum silicate materials are resistant to acid solutions while many core materials (e.g. some metals and many metal oxides) are converted to soluble species suitable for analysis by ICP-MS by exposure to acids such as nitric acid or hydrochloric acid. For particles that comprise polymers, organic solvents may selectively dissolve the polymer (e.g. polystyrene can be dissolved with tetrahydrofuran). Separation of the soluble from insoluble components can be performed by techniques such as centrifugation or filtration to allow for independent analysis of the different components. In some embodiments, these techniques can be utilized to determine the relative percentages of silicon oxide or aluminum in the shell or the amount of metal present in the core.

To identify the organization or structure of the elemental components in some embodiments, X-ray powder diffraction can be utilized.

To identify the organic components of some embodiments, CHN combustion analysis can be employed. Dried samples are analyzed by a CHN analyzer to determine the mass of C, H and N in the sample. Further identification of R groups can be performed by infra-red spectroscopy.

Referring back to FIGS. 1A and 1B, the core 100 of the particle comprises a material that can be a single element or a combination of elements. In an embodiment, the core material can be a metal. Metals utilized for the core include gold, silver, platinum, palladium, copper, aluminum, nickel, iron or mixtures of these metals. Alloys of these metals including gold/silver alloys are considered. In one embodiment, the metal core is a core/shell configuration which includes gold coated silver, silver coated gold and other combinations of metal core/metal shells. In one embodiment, a silver particle is coated with a shell of gold where the gold thickness is less than 50 nm, 20 nm, 10 nm, 5 nm, 3 nm, 2 nm or 1 nm. In another embodiment, a gold particle is coated with a shell of silver where the silver thickness is less than 100 nm, 50 nm, 30 nm, 20 nm, 10 nm or 5 nm.

In an embodiment, the core can approximate various shapes such as spheres, spheroids, ellipsoids, pyramids, prisms, cubes, plates, discs, rods, or hollow spheres. The core can also have non-regular shapes or may be fractal in nature. The core can be fully or partially hollow (e.g., hollow gold particles or hollow silver particles) or be nanoshells where the interior of the particle is a dielectric and the shell is a metal (e.g., gold nanoshells or silver nanoshells). The core can be solid or can be porous. In one embodiment the core is gas or liquid. In one embodiment the liquid core is the same liquid as the suspending liquid.

In an embodiment, the core can be an inorganic oxide or a combination of inorganic oxides including $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$, or $Bi_2O_3$. In an embodiment, the core material is a polymer including but not limited to polystyrene, poly(methyl methacrylate), polybutadiene, polychloroprene, nitrile rubber, acrylic rubber, PTFE, polyvinyl acetate, styrene-butadiene, vinyl acetate-ethylene, PVC, and fluoroelastomer.

Particles Incorporating Functional Entities

In various embodiments of particles having a core and at least one shell described herein with respect to FIGS. 3A-7C, the particles can incorporate various functional entities within the particles. As used herein, a functional entity generally refers to atoms, molecules, clusters, nanoparticles or combinations thereof that can impart various functionalities to the particles. For example, an optical entity described herein refers to an entity that can be detected using optical methods. An optical entity may be, for example, a light emitting entity that can absorb an incident photon of light and emit a second photon of light at a lower energy than the incident photon of light. In another example, an optical entity may be a plasmon resonance entity that can establish a surface plasmon resonance (SPR) condition, which can be established when the frequency of incident light photons matches the natural frequency of surface electrons of metallic structures oscillating against the restoring force of positive nuclei of the metallic structures. The SPR condition can be used for optical measurements such as fluorescence, Raman scattering, second harmonic generation, and absorption, among others. In yet other examples, an entity may be a superparamagnetic entity, a paramagnetic entity or a ferromagnetic entity.

In the following, various entities and particles incorporating the same are described. In some embodiments, particles incorporate functional entities such as light emitting entities. In an embodiment, two or more nanoparticles are incorporated within each particle. In an embodiment, two or more quantum dots, magnetic nanoparticles, up-converting or down-converting nanoparticles, light emitting entities, gold nanoparticles, silver nanoparticles, aluminum nanoparticles or copper nanoparticles are incorporated within each particle. In another embodiment superparamagnetic, paramagnetic or ferromagnetic nanoparticles are incorporated within each particle. In one embodiment there is at least 1, 2, 5, 10 or 20, 100 or 1000 or 10,000 nanoparticles are incorporated within each particle.

Figure 3A:
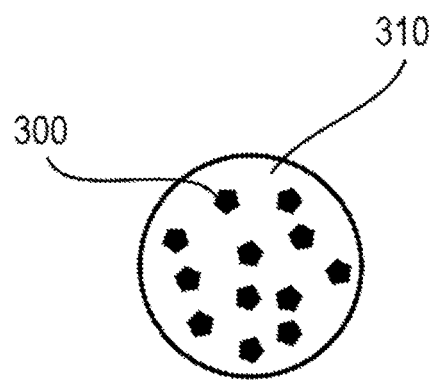
FIG. 3A is a schematic cross-sectional view of a particle core that includes dispersed functional entities, according to some embodiments.

FIG. 3A is a schematic cross-sectional view of a particle core that includes dispersed functional entities, according to some embodiments. In the illustrated embodiment, two or more nanoparticles 300 are incorporated within the core 310 of the particle and are separated from adjacent nanoparticles by the core material. In one embodiment at least 20%, 50%, 70%, 90%, 95% or 98% of the nanoparticles in the core have an edge-to-edge spacing of at least 1 nm, 2 nm, 3 nm, 5 nm, 10 nm or 20 nm. The "edge-to-edge" spacing is defined to be the shortest line between the outer edge of any point on one nanoparticle's surface to any point on the outer edge of another nanoparticle's surface.

Figure 3B:
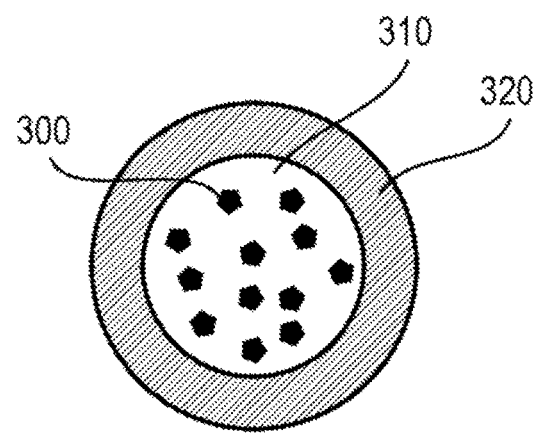
FIG. 3B is a schematic cross-sectional view of the particle core of FIG. 3A that is encapsulated with a shell, according to some embodiments.

FIG. 3B is a schematic cross-sectional view of the particle core of FIG. 3A that is encapsulated with a shell, according to some embodiments. In FIG. 3B, the core 310 having nanoparticles 300 dispersed therein is encapsulated by an aluminum silicate shell 320. In some embodiments, the nanoparticles 300 are uniformly dispersed throughout each particle.

Figure 4A:
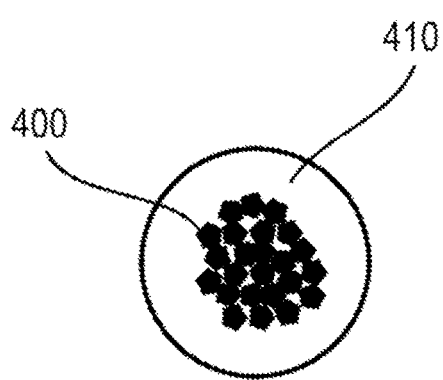
FIG. 4A is a schematic cross-sectional view of a particle core that includes aggregated functional entities, according to some embodiments.

FIG. 4A is a schematic cross-sectional view of a particle core that includes aggregated nanoparticles, according to some embodiments. In the illustrated embodiment, a cluster of nanoparticles 400 is encapsulated within a core 410. In one embodiment there is at least 1, 2, 5, 10 or 20, 100 or 1000 or 10,000 nanoparticles in the cluster. In another embodiment at least 20%, 50%, 70%, 90%, 95% or 98% of the nanoparticles in the core have an edge-to-edge spacing that is less than 10 nm, 5 nm, 3 nm, 2 nm or 1 nm. In yet another embodiment, at least some of the nanoparticles 400 are in contact with one another.

Figure 4B:
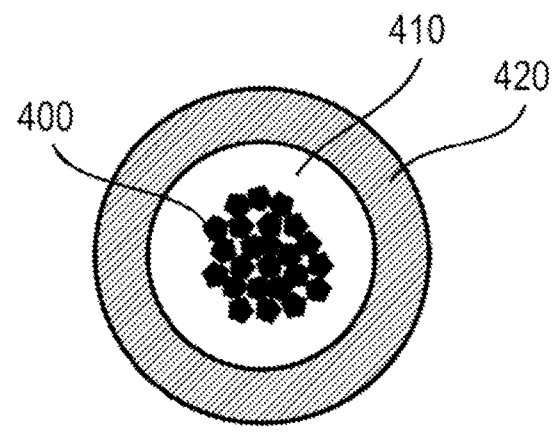
FIG. 4B is a schematic cross-sectional view of the particle core of FIG. 4A that is encapsulated with a shell, according to some embodiments.

FIG. 4B is a schematic cross-sectional view of the particle core of FIG. 4A that is encapsulated with a shell, according to some embodiments. In the illustrated embodiment, the core 410 having the nanoparticles 400 encapsulated therein is further encapsulated by an aluminum silicate shell 420.

In some embodiments, functional entities incorporated in the particles are quantum dot nanoparticles that are incorporated within the core, within one or more shells or bound to the surface of the core or shells. As described herein, without being bound to any theory, quantum dots refer to semiconductor nanoparticles in which carriers (e.g., electrons, holes, excitons) are physically confined within a physical dimensions that is smaller than a critical size (e.g., electronic Bohr radius) such that the energy levels (e.g., band-to-band recombination energy) of the carriers change. As a result, a quantum dot of a semiconductor material has an absorption or an emission wavelength that can be lower (i.e., higher energy) than a bulk semiconductor having the same composition as the quantum dot. Some quantum dots can have a core-shell structure of their own. In these configurations, for example, a core of a quantum dot can have a lower band gap energy compared to a shell of the quantum dot such that a radial quantum well can be formed. As used herein, a quantum dots refer to semiconductor nanoparticles that can emit light having a peak wavelength at least 10 nanometers shorter than an emission wavelength of a bulk semiconductor material having the same composition as the semiconductor material.

In various embodiments described herein, quantum dots can be semiconductor nanoparticles that comprise, e.g., a core of Si, Ge, CdS, CdSe, CdTe, ZnS, ZnSe, ZnTe, GaAs, GaP, GaAs, GaSb, HgS, HgSe, HgTe, InAs, InP, InSb, AlAs, AlP, AlSb, an alloy thereof, or a mixture thereof, and are, optionally, over coated with a shell material comprising a material different from the nanoparticle core material. In one embodiment the quantum dot shell material comprises ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, AlSb, an alloy thereof, or a mixture thereof. However, the materials of the core and the shell can be interchanged. Preferably, the band gap energy of the over coating is greater than that of the core. When illuminated with light of a wavelength that is absorbed by the quantum dots, the quantum dots emit light with a peak wavelength 10 or more nanometers greater than that of the incident light. The core or core-shell semiconductor quantum dots may be further coated with a material having an affinity for a surface. In a particular embodiment, this coating material may comprise a carboxylic acid. In an embodiment, quantum dots functionalized with carboxylic acids are covalently bound to an aluminum silicate shell that has amine containing R groups. In a preferred embodiment the carboxylic acid on the quantum dot is lipoic acid.

In an embodiment, incorporated functional entities are up-converting nanoparticles and are incorporated within the core, within one or more shells or bound to the surface of the core or shells. Without being bound to any theory, photon upconversion (UC) refers to a process in which the sequential absorption of two or more photons leads to the emission of light at shorter wavelength than the excitation wavelength. Upconverting nanoparticles include lanthanide doped nanoparticles and other rare-earth doped nanoparticles. Down-converting nanoparticles emit light at longer wavelengths than the absorbed light.

In an embodiment, incorporated entities are plasmonic nanoparticles and are incorporated within the core, within one or more shells or bound to the surface of the core or shells. Plasmonic nanoparticles are particles whose electron density can couple with electromagnetic radiation of wavelengths that are larger than the particle due to the nature of the dielectric-metal interface between the medium and the particles resulting in strongly enhanced light absorption and scattering cross-sections. In some embodiments, plasmonic particles comprise gold, silver, copper or aluminum metals or combinations of these.

Without being bound to any theory, the plasmonic nanoparticle's interaction with light is affected by the proximity of one plasmonic particle to another. In some embodiments the plasmonic nanoparticles are close enough together that their optical properties are affected by other plasmonic nanoparticles. In some embodiments the plasmonic nanoparticles are sufficiently separated that they are not influenced by neighboring particles. In one embodiment the plasmonic particles are in contact or have median edge-to-edge spacings of less than 2 nm, 5 nm, 10 nm, 20 nm, 50 nm, or 100 nm. In other embodiments, the median edge-to-edge spacing is greater than 5 nm, 10 nm, 20 nm, 50 nm, or 100 nm.

In an embodiment, incorporated functional entities are magnetic nanoparticles are incorporated within the core, within one or more shells or bound to the surface of the core or shells. Magnetic nanoparticles have a magnetic response in a magnetic field. In some embodiments, this response may take the form of being attracted to a magnet allowing for separation of the particles from a fluid, changing the spacing between the particles to effect a change in the interaction of the particles with light, or to induce changes in the nuclear resonance of surrounding nuclei such that they can be used as a contrast agent for nuclear magnetic resonance imaging. In one embodiment, the magnetic nanoparticles are chosen from a group consisting of iron, cobalt, nickel, gadolinium or dysprosium and their associated oxides. In another embodiment, the magnetic nanoparticles comprise any other elements or combination of elements that are ferromagnetic. In an embodiment, the magnetic nanoparticles are comprised of particles with a median diameter that is less than 130 nm, less than 100 nm, less than 50 nm, less than 40 nm, less than 30 nm, or less than 20 nm. In an embodiment, the magnetic nanoparticles have a median size between 5 nm and 50 nm or 5 nm and 100 nm. In an embodiment, the magnetic nanoparticles are superparamagnetic. In a preferred embodiment the magnetic nanoparticles are comprised of at least 30%, 50%, 70%, or 90% of iron oxide of the formula $Fe_3O_4$ or $Fe_2O_3$. In an embodiment, the magnetic nanoparticles have an average magnetic moment of at least 1 emu/g, 2 emu/g, 5 emu/g, 10 emu/g, 30 emu/g or 100 emu/g in a field of 20000 Oe.

In an embodiment, light emitting entities (LEEs) are incorporated within the core, within one or more shells or bound to the surface of the core or shells. LEEs include fluorophores, dyes, luminophores, chemiluminescent species, or phosphors. "Fluorophore," as used herein, means any substance that emits electromagnetic energy such as light at a certain wavelength (emission wavelength) when the substance is illuminated by radiation of a different wavelength (excitation wavelength). Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalog. In an embodiment, the LEEs are organic fluorescent dyes that emit light in the visible to near infrared light of wavelength in the range of 400 to 900 nm when excited by ultraviolet to near infrared light of wavelength in the range of 200 to 700 nm. The organic fluorescent dyes include fluorescein type dye molecules, rhodamine type dye molecules, Alexa Fluor (produced by Invitrogen Corp.) type dye molecules, BODIPY (produced by Invitrogen Corp.) type dye molecules, cascade type dye molecules, coumarin type dye molecules, eosin type dye molecules, NBD type dye molecules, pyrene type dye molecules, Texas Red type dye molecules, cyanine type dye molecules, and the like. Specific examples of the organic fluorescent dye include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethyl rhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (the above produced by Invitrogen Corp.), methoxycoumarin, eosin, NBD, pyrene, Cy 5, Cy 5.5, Cy 7, or the like. Such organic fluorescent dyes may be used singly or in combination of multiple types. The fluorophores may be evenly distributed, have a gradient in concentration, or be randomly distributed within or on the cores or shells.

Referring to FIGS. 5A-5E, in various embodiments, functional entities can be bound to the surface of a core, surface of a shell or be incorporated within a shell. In an embodiment, the functional entities are two or more quantum dots, up-converting or down-converting nanoparticles, plasmonic nanoparticles, magnetic nanoparticles, or LEEs. In one embodiment there are at least 1, 2, 5, 10 or 20, 100 or 1000 functional entities bound to the surface of the core.

Figure 5A:
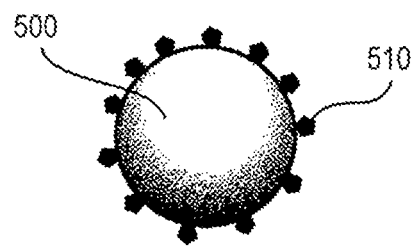
FIG. 5A is a schematic cross-sectional view of a particle core having functional entities formed on its surface, according to some embodiments.

FIG. 5A is a schematic cross-sectional view of a particle core having functional entities formed on its surface, according to some embodiments. In the illustrated embodiment, a core 500 has functional entities bound to the surface 510 of the core. In some embodiments the core 500 is polystyrene, silica, titanium dioxide, aluminum oxide, latex, polyacrylamide, or another polymer or oxide. In some embodiments, the binding of the functional entities to the core is electrostatic, covalent or due to physisorption. In one embodiment, the functional entities are quantum dots that have been bound to the surface of the particle via electrostatic or covalent binding. In one embodiment, the quantum dots are bound to an amine functionalized core surface via one or more amide bonds. In another embodiment, an aluminum silicate-shelled particle that has one or more quantum dots attached to the surface of the particle is functionalized with targeting biomolecules such as peptides, DNA or antibodies. In another embodiment, the particle is further coated with proteins (for example, BSA or casein).

Figure 5B:
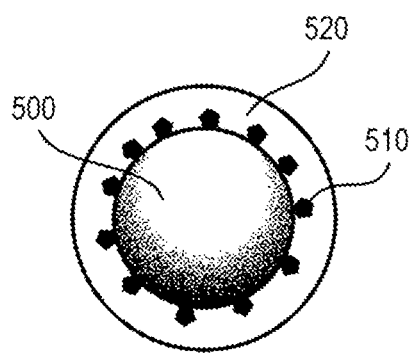
FIG. 5B is a schematic cross-sectional view of a particle having a core, a shell encapsulating the core, and functional entities formed at the core-shell interface, according to some embodiments.

FIG. 5B is a schematic cross-sectional view of a particle having a core, a shell encapsulating the core, and functional entities formed at the core-shell interface, according to some embodiments. In the illustrated embodiment, an aluminum silicate shell 520 encapsulates functional entities 510 bound to the surface 500 of the core. In one embodiment, the aluminum silicate shell is further functionalized with molecules such as proteins, antibodies, or DNA.

Figure 5C:
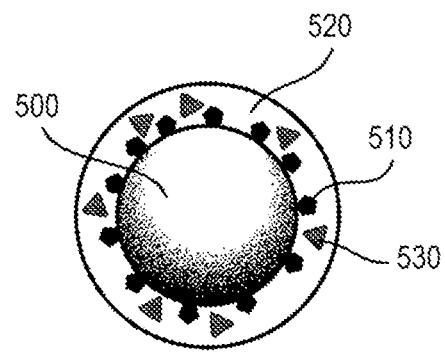
FIG. 5C is a schematic cross-sectional view of a particle having a core that is encapsulated with a shell having dispersed functional entities therein, according to some embodiments.

FIG. 5C is a schematic cross-sectional view of a particle having core that is encapsulated with a shell having dispersed functional entities therein, according to some embodiments. In the illustrated embodiment, an aluminum silicate shell 520 encapsulates a core 500. In addition, functional entities 530 are dispersed throughout the shell and, optionally, functional entities 510 bound to the surface of the core. In one embodiment, at least 20%, 50%, 70%, 90%, 95% or 98% of the nanoparticles in the shell have an edge-to-edge spacing of at least 1 nm, 2 nm, 3 nm, 5 nm, 10 nm or 20 nm.

Figure 5D:
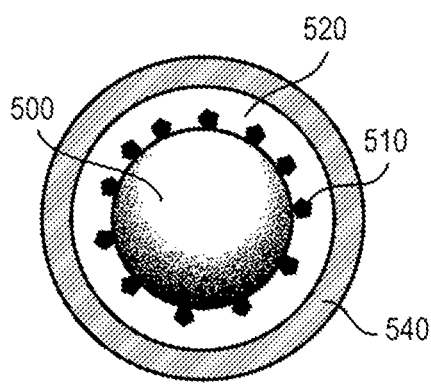
FIG. 5D is a schematic cross-sectional view of a particle having a core, a first shell encapsulating the core, functional entities formed at the core-shell interface and a second shell encapsulating the first shell, according to some embodiments.

FIG. 5D is a schematic cross-sectional view of a particle having a core, a first shell encapsulating the core, functional entities formed at the core-shell interface and a second shell encapsulating the first shell, according to some embodiments. In the illustrated embodiment, a core 500 with functional entities 510 bound to the surface of the core is encapsulated with an intermediate shell 520. The particle of FIG. 5D is further encapsulated with a second shell that comprises aluminum silicate 540. In an embodiment, the intermediate shell comprises a material different than the core and the aluminum silicate outer shell. In an embodiment, the intermediate shell comprises a material that is the same as the core and the aluminum silicate outer shell.

Figure 5E:
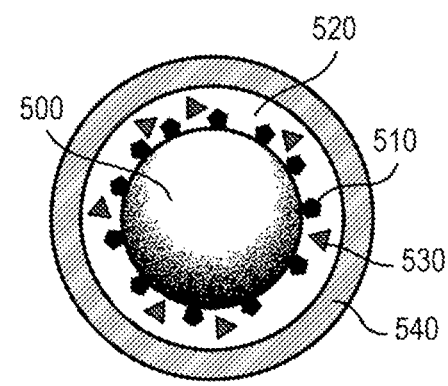
FIG. 5E is a schematic cross-sectional view of a particle having core that is encapsulated with a first shell having dispersed functional entities therein, and a second shell encapsulating the first shell, according to some embodiments.

FIG. 5E is a schematic cross-sectional view of a particle having core that is encapsulated with a first shell having dispersed functional entities therein, and a second shell encapsulating the first shell, according to some embodiments. In the illustrated embodiment, a core 500 with functional entities 530 dispersed in an intermediate shell 520 and, optionally, functional entities 510 bound to the surface of the core is encapsulated with a second shell that comprises aluminum silicate 540. In one embodiment at least 20%, 50%, 70%, 90%, 95% or 98% of the functional entities in the intermediate shell have an edge-to-edge spacing of at least 1 nm, 2 nm, 3 nm, 5 nm, 10 nm or 20 nm. In an embodiment, the binding of functional entities to the surface of the core or shell can occur via electrostatic binding or via covalent coupling. Examples of covalent binding chemistry include but are not limited to bond formations between carboxylic acid and amine functionalized surfaces, or amine and sulfhydryl surfaces. The intermediate shell or final shell can have a thickness that is less than 200 nm, less than 100 nm, less than 50 nm, less than 20 nm or less than 10 nm.

Figure 6A:
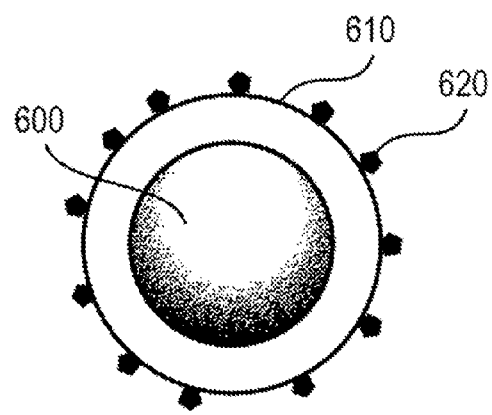
FIG. 6A is a schematic cross-sectional view of a particle having a core and a shell encapsulating the core and having functional entities formed on its surface, according to some embodiments.
Figure 6B:
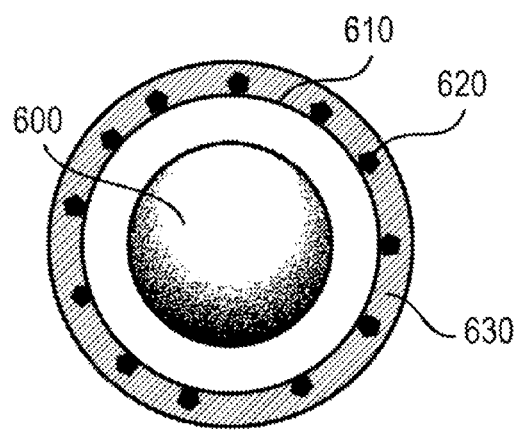
FIG. 6B is a schematic cross-sectional view of a particle having a core, a first shell encapsulating the core, a second shell encapsulating the first shell and functional entities formed at the interface between the first shell and the second shell, according to some embodiments.
Figure 6C:
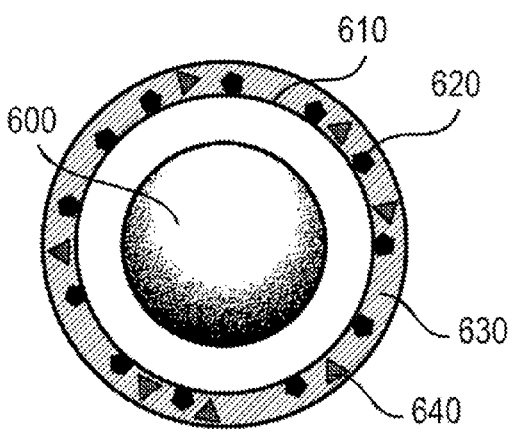
FIG. 6C is a schematic cross-sectional view of a particle having a core, a first shell encapsulating the core and a second shell encapsulating the first shell and having functional entities dispersed therein, according to some embodiments.

Referring to FIGS. 6A-6C, in various embodiments, functional entities can be bound to the surface of an inner shell, formed at an interface between the inner shell and an outer shell, or be incorporated within the outer shell.

FIG. 6A is a schematic cross-sectional view of a particle having a core and a shell encapsulating the core and having functional entities formed on its surface, according to some embodiments. In the illustrated embodiment, a core 600 is encapsulated with a shell 610. In an embodiment, the core is a polymer, metal, or metal oxide and the core is encapsulated with a shell material that is different from the core material. In an embodiment, the shell material is a polymer, metal, or metal oxide. In an embodiment, the core is silicon oxide and the shell is aluminum silicate. In an embodiment, the shell can have a thickness that ranges from 1 nm to 200 nm, 1 nm to 100 nm, or 1 nm to 50 nm. In another embodiment, the shell can have a thickness that is less than 200 nm, less than 100 nm, less than 50 nm, less than 20 nm or less than 10 nm. In some embodiments, functional entities 620 are bound to the surface of the shell. In an embodiment, the functional entities are two or more quantum dots, up-converting or down-converting nanoparticles, plasmonic nanoparticles, magnetic nanoparticles, or LEEs.

FIG. 6B is a schematic cross-sectional view of a particle having a core, a first shell encapsulating the core, a second shell encapsulating the first shell and functional entities formed at the interface between the first shell and the second shell, according to some embodiments. In the illustrated embodiment, a core coated with an intermediate shell 610 has functional entities bound to the surface of the shell 620 and is further encapsulated with an aluminum silicate shell 630. In an embodiment, the intermediate shell is aluminum silicate and the outer shell is aluminum silicate.

FIG. 6C is a schematic cross-sectional view of a particle having a core, a first shell encapsulating the core and a second shell encapsulating the first shell and having functional entities dispersed therein, according to some embodiments. In the illustrated embodiment, a core particle 600 coated with an intermediate shell 610 is further encapsulated with an aluminum silicate shell 630 that contains functional entities 640 dispersed within the shell and, optionally, functional entities 620 bound to the first shell. In one embodiment the functional entities are two or more quantum dots, up-converting or down-converting nanoparticles, plasmonic nanoparticles, magnetic nanoparticles, or LEEs. The intermediate or outer shell can have a thickness that is less than 200 nm, less than 100 nm, less than 50 nm, less than 20 nm or less than 10 nm.

In another embodiment, the particles comprises a core and multiple shells where two or more quantum dots, up-converting or down-converting nanoparticles, plasmonic nanoparticles, magnetic nanoparticles, or LEEs are incorporated in the core, on the surface of the core, in one or more of the shells, or on the surface of one of more of the shells and where at least one of the shells is aluminum silicate. In an embodiment, the core or shells can be a metal, metal oxide or polymer. In an embodiment, the core or shells comprise gold, silver, silica, aluminum silicate, titanium dioxide, zinc oxide, polystyrene, latex, or polyacrylamide.

In another embodiment, the particles comprises a core and one or more shells where nucleic acids or proteins, are incorporated in the core, on the surface of the core, in one or more of the shells, or on the surface of one of more of the shells and where at least one of the shells is aluminum silicate. In one embodiment the nucleic acids are DNA or RNA and are incorporated at a mass percentage of at least 0.001%, 0.01%, 0.03%, 0.05%, 0.1%, 0.3%, 1% of the mass of the particle. In one embodiment the nucleic acids are electrostatically bound to the shell. In one embodiment the nucleic acids are incorporated within the core or the intermediate shell and not the final shell. In one embodiment the core or one of the shells contains magnetic nanoparticles and one or more shells contain nucleic acids.

Particle Surface Functionalization

In the following, various embodiments of particles in which a surface of a core and/or a shell having functional entities and/or bifunctional or linker molecules attached thereto are described with respect to FIGS. 7A-7C. In various embodiments, the surface of the particle 210, 220, 310, 320, 410, 420, 510, 520, 540, 550, 560, 610, 620, 630 and 650 can be functionalized with molecules.

Figure 7A:
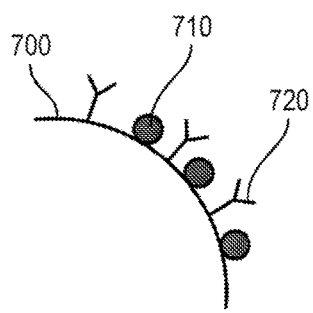
FIG. 7A is a schematic representation of a surface of a core and/or a shell of a particle having functional entities and/or bifunctional or linker molecules attached thereto, according to some embodiments.

FIG. 7A is a schematic representation of a surface of a core and/or a shell of a particle having functional entities and/or bifunctional or linker molecules attached thereto, according to some embodiments. In the illustrated embodiment, molecules 720 are bound to the aluminum silicate surface 700.

Figure 7B:
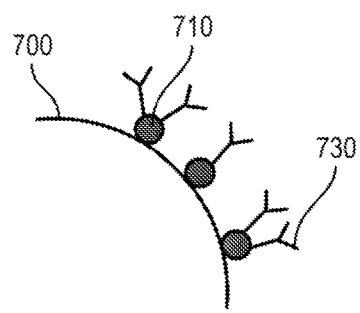
FIG. 7B is a schematic representation of a surface of a core and/or a shell of a particle having functional entities attached thereto, and bifunctional or linker molecules attached to the entities, according to some embodiments.

FIG. 7B is a schematic representation of a surface of a core and/or a shell of a particle having functional entities attached thereto, and bifunctional or linker molecules attached to the entities, according to some embodiments. In the illustrated embodiment, molecules 730 are bound to an entity 710 that is bound to the aluminum silicate surface 700.

Figure 7C:
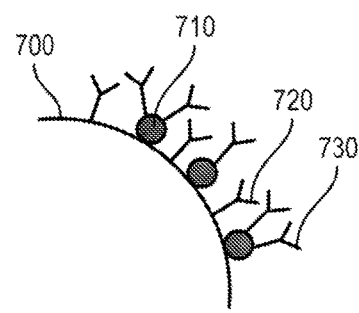
FIG. 7C is a schematic representation of a surface of a core and/or a shell of a particle having functional entities and bifunctional or linker molecules attached thereto, and further having bifunctional or linker molecules attached to the functional entities, according to some embodiments.

FIG. 7C is a schematic representation of a surface of a core and/or a shell of a particle having functional entities and bifunctional or linker molecules attached thereto, and further having bifunctional or linker molecules attached to the functional entities, according to some embodiments. In the illustrated embodiments, molecules 720, 730 are bound to both the aluminum silicate surface 700 and functional entities that are bound to the aluminum silicate surface 710. In one embodiment, there is one type of molecule bound to the surface of the aluminum silicate 700 and a different type of molecule bound to the surface of the entity bound to the aluminum silicate surface 710.

In various embodiments, the functional entities can be any one or more of quantum dots, up-converting or down-converting nanoparticles, plasmonic nanoparticles, magnetic nanoparticles, or LEEs. In one embodiment the molecules are polymers. In one embodiment, the molecules are one or more types of polyethylene glycol (PEG). PEG comprises a linear oligomer of ethylene glycol of the form $(-CH_2CH_2O-)_x$ where x is in the range of 2 to 2000 and the $CH_2CH_2$ groups are linked in a chain. In a preferred embodiment, there is a mixture of functionalized PEG molecules and non-reactive PEG molecules bound to the surface 700 or the functional entities 710 that can be further reacted with other molecules and PEG molecules that do not have an active binding site. In one embodiment the PEG molecules are a mixture of methoxy PEG (PEG-OMe) and carboxylic acid PEG (PEG-COOH) and the ratio between PEG-OMe and PEG-COOH is in the range of 1:1 to 1:2, 1:1 to 1:3, 1.1 to 1:5, 1:1 to 1:10, 1:1 to 1:100, 1:3 to 1:10, 1:3 to 1:50, or 1:5 to 1:50. In another embodiment, the PEG molecules are linked to the particle surface via one end of a heterobifunctional linker. N-hydroxysuccinimide-PEG-maleimide is non-limiting example of one such PEG molecule where one end of the molecule has an affinity for amines. In one embodiment, one end of a PEG molecule has an affinity for amines on the aluminum silicate surface and the other end of the PEG molecule has an affinity for a free thiol group of an antibody. In other embodiments, the PEG molecules are incorporated via silane chemistry. $PEG-CH_2CH_2NC(O)NHCH_2CH_2Si(OEt)_3$ is one non-limiting example of a silane PEG molecule that can be bonded to an aluminum silicate surface via bridging oxygens of a hydrolyzed silane. In one embodiment the binding of the PEG molecule is via EDC coupling, click chemistry, hyNic/4FB binding such as available from Solulink, and other bifunctional linkers known to those skilled in the art.

In one embodiment the nanoparticle may be further functionalized with a targeting moiety. As used herein, the term "targeting moiety" may include, but is not limited to, any molecule that has specificity to an antigen, an antibody, a protein, a particle, a virus, a crystallographic orientation, or a marker expressed by a cell or pathogen, either extracellularly (e.g., on the cell surface or secreted by the cell) or intracellularly. In certain embodiments, the targeting moiety is specific for an antigen such as a tumor antigen or acts as a probe used in an assay such as a plate assay, a microscope-based assay or a lateral flow assay. In other embodiments, the targeting moiety is specific for a pathogenic antigen. The targeting moiety may include, but is not limited to, antibodies and fragments thereof, haptens, polypeptides, oligonucleotides, DNA, anti-sense RNA, peptide nucleic acids, proteins, chimeric and/or fusion proteins, and the like.

The targeting moiety may be attached to the surface of the coated nanoparticle via a linker. The targeting moiety can be attached by any stable physical or chemical association to the surface coating directly or indirectly by any suitable means (e.g., covalent bond, non-covalent bond, electrostatic charge and the like).

Direct linking of the targeting moiety implies only that functional groups on the coating surface of the particle and the targeting moiety itself serve as the points of chemical attachment. In such instances, the surface coating can be modified by functional organic molecules with reactive groups such as thiols, amines, carboxyls, and hydroxyl. The surface active reactants include, but are not limited to, aliphatic and aromatic amines, mercaptocarboxylic acid, carboxylic acids, aldehydes, amides, chloromethyl groups, hydrazide, hydroxyl groups, sulfonates and sulfates to accommodate such direct linkages.

In another embodiment the aluminum silicate particles may be incorporated into any kind of vehicle that is normally used for cosmetic compositions. For example, the metallic particles can be added to solutions, colloidal dispersions, emulsions (oil-in-water or water-in-oil), suspensions, powders, foundations, creams, lip creams, lotions, gels, foams, mousses, sprays and the like. Methodology for formulation of different vehicle types can be found for example in Remington's The Science and Practice of Pharmacy, 19th Edition, Volume II.

In one embodiment, the aluminum silicate particles may be used as a reporter in biological systems. In one embodiment the aluminum silicate-shelled particles contain LEEs. Aluminum silicate-shelled particles can be used in diagnostic assays such as ELISAs, lateral flow assays, immunostaining, immunohistology, immunochemistry, and microarrays. In one embodiment, the core of the particle is a plasmonic material and one or more of the shells contains LEEs. In one embodiment the core of the particle is a dielectric and the intermediate shell is gold or silver and LEEs are incorporated within the outer aluminum silicate shell. In one embodiment, the core is silver or gold and quantum dots are embedded within or attached to the surface of one or more of the shells. In one embodiment the core is silica, at least one of the shells is aluminum silicate and one or more quantum dots are embedded within or attached to the surface of one or more of the shells. In one embodiment the core is silicon oxide and the surface of the core is converted to an aluminum silicate shell by exposure to an aluminum salt. In one embodiment, an amine functionalized aluminum silicate shell fabricated by the exposure of a silicon oxide core to solution of aluminum chloride is functionalized with a plurality of quantum dots. In one embodiment, the plasmon resonant wavelength of the core particle overlaps with either the excitation or emission wavelength of the LEEs that are incorporated into one or more of the shells.

In one embodiment, magnetic aluminum silicate particles can be used to isolate or separate compounds, analytes, or molecules from solution. In one embodiment magnetic aluminum silicate particles are used to extract DNA, antigens, or trace metals from solution.

In another embodiment, the particles consists of a core and one or more shells where nucleic acids or proteins, are incorporated in the core, on the surface of the core, in one or more of the shells, or on the surface of one of more of the shells and where at least one of the shells is aluminum silicate. In one embodiment the nucleic acids are DNA or RNA and are incorporated at a mass percentage of at least 0.001%, 0.01%, 0.03%, 0.05%, 0.1%, 0.3%, or 1% of the mass of the particle. In one embodiment the nucleic acids are electrostatically bound to the shell. In one embodiment the nucleic acids are incorporated within the core or the intermediate shell and not the outer shell. In one embodiment, the core or one of the shells contains magnetic nanoparticles and one or more shells contain nucleic acids. In one embodiment, magnetic aluminum silicate shelled particles contain nucleic acids with a median length in the range of 10 to 2000, 20 to 1000, 20 to 500, or 30 to 500 nucleotides. In one embodiment, the nucleic acid containing particles are released into the environment and then subsequently recovered and analyzed by dissolving the particles, using the polymerase chain reaction and detecting the amplified product of the released nucleic acid. In one embodiment, the nucleic acid containing particles are integrated into rivers, lakes, ground water, soil. In another embodiment, the nucleic acid containing particles are incorporated into commercial products such as explosives, paints, inks, food, pharmaceuticals, or currency to determine the product's authenticity or origin. In another embodiment the nucleic acid containing particles are fabricated to withstand high temperatures (at least 60° C., 80° C., 100° C. or 120° C.), in an acidic (pH between 2 and 5, pH between 2 and 6, pH between 2 and 7) or basic (pH between 8 and 11, pH between 8 and 12, pH between 9 and 12) environments for 1, 2, 5, 10 or 20 days where at least 20%, 40%, 60%, 80%, 90% or 95% of the nucleic acid is retained in the particle. In another embodiment, magnetic nucleic acid containing particles are extracted from a liquid or a dissolved solid by using a magnetic field. In one embodiment, an apparatus is utilized that flows the liquid over a magnet where the liquid film has a thickness of less than 1, 2, 5, or 10 mm. In another embodiment, the nucleic acid is released from the particle by dissolving the particles in an aqueous fluoride solution.

In one embodiment, aluminum silicate particles that contain clusters of magnetic nanoparticles in their core are used for generating optical colors and optical patterns when exposed to a magnetic field. In an embodiment, the magnetic aluminum silicate particles have a diameter that has a coefficient of variation (standard deviation divided by the mean) of less than 30%, 20%, 15%, 12% or 10%. In an embodiment, magnetic aluminum silicate particles are coated with a shell of gold or silver. In an embodiment, the magnetic aluminum silicate particles are suspended in water at a mass concentration of at least 0.1%, 0.2%, 0.5%, 1%, 2%, 3%, 5%, or 10%.

In an embodiment, aluminum silicate particles with a silver nanoplate core are used as a continuous use indicator to determine how long a surface or composite has been exposed to water or salt water. In one embodiment, the aluminum silicate nanoplate particles are incorporated into a silicone material. In one embodiment, the aluminum silicate nanoplate particles are used as a continuous use monitor for needle-less connectors, IV bags, and/or IV set components. In another embodiment, the aluminum silicate-shelled nanoplates are used as strike through indicators for bandages.

In an embodiment, the core is hollow and one or more shells are aluminum silicate. In an embodiment, the interior volume of the core and the interstitial volume of the porous aluminum silicate shell contains absorbed molecules. In one embodiment, the absorbed molecules are drugs, dyes, or catalysts. In one embodiment the hollow aluminum silicate particles are functionalized with targeting ligands to deliver therapeutic drugs to a specific region of the body.

In an embodiment, a silicon oxide core encapsulated with an aluminum silicate shell is coated with a plurality of gold nanoparticles that have an average diameter less than 10 nm bound to the aluminum silicate surface. In an embodiment, a silicon oxide core encapsulated with an aluminum silicate shell is coated with a partial or complete shell of gold to form a gold nanoshell. In an embodiment, a silicon oxide core encapsulated with an aluminum silicate shell is coated with a partial or complete shell of silver to form a silver nanoshell. In an embodiment, a silicon oxide core encapsulated with an aluminum silicate shell is coated with a plurality of gold nanoparticles and further encapsulated with a silver shell.

Methods of Preparing Particles Having a Core-Shell Structure

Core nanoparticles made from metal or metal oxide cores can be produced by various methods. In one embodiment metal core nanoparticles are produced by the reduction of metal salts in the presence of stabilants such as sodium citrate, polyvinylpyrollidone, cetyl trimethylammonium bromide, ascorbic acid. Metal and metal oxide cores can be fabricated with shapes that approximate spheres, pyramids, triangles, cubes, plates, discs, wires, rods, and fractals. The metal core nanoparticles can be hollow (e.g. hollow gold or hollow silver) or be nanoshells where the interior of the particle is a dielectric and the shell is a metal (e.g. gold nanoshells or silver nanoshells).

In one embodiment, a coupling agent is bound to the surface of the metal or metal oxide core particle before the growth of the silicon oxide shell. Coupling agents can include mercaptoundecanoic acid, mercaptoprionic acid, polyvinylpyrollidone, polyvinyl alcohol, aminopropyltrimethoxy silane, mercaptopropyltrimethoxy silane, or other amino or mercapto containing silanes. In some embodiments, the coupling agent is added at a concentration to provide at least 10%, 20%, 50%, 100%, 200%, 500%, 1000%, 10000% monolayer coverage of the core particles. In some embodiments, the core nanoparticles are transferred to an alcohol based solvent. The transfer to a different solvent can occur using centrifugation or tangential flow filtration.

In an embodiment, the particles are coated in solution utilizing precursors including species of the formula $X_n Si Y_{(4-n)}$ where $0<n<4$; and X and Y are each independently OEt, OMe, Cl, Br, I, H, alkyl, fluoroalkyl, perfluoroalkyl, alkoxide, aryl, alkyl amine, alkyl thiol or any combination thereof. In another embodiment, the silicon oxide shell is produced using silanes or mixtures of silane molecular units that have the formula $Si(R_{1-4})_4$ where $R_1$, $R_2$, $R_3$, and $R_4$ can be various functional groups include methyl, ethyl, propyl or other alkyl molecules, alkyl amines, alkyl thiols, alkyl carboxylic acids or other combinations of molecules as are found in commercially available silanes from chemical supply companies such as Gelest (Morrisville, Pa.). Some embodiments comprise mono-, di-, or tri-functional chlorosilanes, alkoxysilane or silasanes. Some embodiments comprise alkylsilanes, dialkylsilanes, polyalkylsilanes, organochlorosilanes, organodichlorosilanes, organopolychlorosilane, oxalkylsilanes, ethenylsilanes, organosilanols, organosilanethiols, organoiodosilanes. In embodiments where the chemical moieties connected to the silicon atom are not hydrolysable, the non-hydrolysable groups give rise to functionality throughout and on the surface of the silicon oxide shells. In one embodiment the silicon oxide shell is fabricated using one or more of aminopropyltriethoxy silane, aminopropyltrimethoxy silane, aminopropyltrimethoxy silane, mercaptopropyl-triethoxysilane, mercapto-propylmethoxysilane, tetramethoxy silane, and tetraethoxy silane. Silanes with one, two, three, or four terminations that can link to other silane molecules are also considered for incorporation into the silicon oxide shell. In another embodiment hydrophobic silicon oxide coatings can be obtained by encapsulating the nanoparticles with a silicon oxide coating formed via the condensation of silane molecules with hydrophobic functional groups. For example, the condensation of fluorosilane derivatives such as (tridecafluoro-1,1,2,2-tetrahydrooctyl) triethoxysilane and (heptadecafluoro-1,1,2,2-tetrahydrodecyl) triethoxysilane onto the surface of the nanoparticles will render the surface of the nanoparticles hydrophobic. In one embodiment the condensation is performed in an alcohol solvent such as ethanol, methanol, butanol, or isopropyl alcohol. In one embodiment the condensation is performed in a basic environment using a basic material such as ammonium hydroxide. In one embodiment, the ratio of the mass of the cores to the mass of the silane is calculated to produce silicon oxide shells that are at least 1 nm, 2 nm, 5 nm, 10 nm, 15 nm, 20 nm or 50 nm thick. In one embodiment the silicon oxide-shelled particles are heated during or after shell formation. In one embodiment the solution is heated to >90° C., >95° C., or >99° C.

In an embodiment, the aluminum silicate shell is formed from the condensation of one or more silanes to form a silicon oxide shell followed by the exposure of the silicon oxide shell to an aluminum moiety. In another embodiment the alumina-silica shell is formed from the condensation of one or more silanes in the presence of an aluminum moiety. Silicon oxide-coated core particles can be exposed to an aluminum moiety which can be in the form of any chemical compound that dissolves to release an aluminum ion. In one embodiment, aluminum salts may be, for example one or more of aluminum acetate, aluminum phosphate monobasic, aluminum sulfate, aluminum ethoxide, aluminum potassium sulfate, aluminum silicate, aluminum acetate, aluminum arsenide, aluminum bromide, aluminum chloride, aluminum chloride hydrate, aluminum fluoride, aluminum fluoride hydrate, aluminum fluoride trihydrate, aluminum hydroxide, aluminum iodide, aluminum sulfide, aluminum nitrate, aluminum thiocyanate, aluminum chlorate, and aluminum nitrite. In one embodiment the aluminum salt or salt solution is added to the nanoparticles that are in the solution used to fabricate the silicon oxide shells. In another embodiment, the silicon oxide-shelled core particles are transferred to another solvent (e.g. water) before the addition of the aluminum moiety. In one embodiment, the aluminum species is present in the particle solution at a concentration of at least 0.01 mM, 0.1 mM, 0.2 mM, 0.3 mM, 1 mM, 2 mM, 5 mM, 10 mM, 20 mM, 50 mM, 100 mM, 200 mM, or 500 mM. In one embodiment, the aluminum ion concentration is in the range of 0.01 mM to 100 mM, 0.1 mM to 100 mM, 1 mM to 100 mM, 0.01 mM to 10 mM, 0.1 mM to 10 mM or 0.1 mM to 1000 mM. In one embodiment, the aluminum chloride is incubated with the core particles for at least 1 min, 2 mM, 5 mM, 10 mM, 30 mM, 60 mM, 2 hrs, 5 hrs, 12 hrs, or 24 hrs. In one embodiment the pH of the incubation solution is adjusted to a specific pH range, for example between 1 and 3, 2 and 4, 3 and 5, 4 and 6, 5 and 7, 6 and 8, 7 and 9, 8 and 10 or 9 and 11. In one embodiment, the aluminum salt and particle solution is heated to at least 30° C., 40° C., 50° C., 70° C., 90° C., 100° C., 120° C. In one embodiment the aluminum chloride concentration is reduced after incubation by washing the particle using multiple centrifugation steps or continuous flow filtration. In some embodiments, the concentration of aluminum chloride is reduced by a factor of at least 2, 3, 5, 10, 30, 100, 300, 1000, or 10000, or 100000 from the original aluminum chloride concentration. In one embodiment, the aluminum silicate-shelled particles are concentrated to a total mass concentration of at least 0.1 mg/mL, 0.2 mg/mL, 0.3 mg/mL, 1 mg/mL, 2 mg/mL, 3 mg/mL, 10 mg/mL, 20 mg/mL, 50 mg/mL or 100 mg/mL for long term storage. In one embodiment, other metal salts that comprise other elements besides aluminum can be utilized to increase the stability of the silicon oxide shells.

In an embodiment, light emitting molecules such as fluorophores, dyes, luminophores, chemiluminescent species, or inorganic nanoparticles such as quantum dots, up converting or down converting nanoparticles, or phosphors are incorporated into the aluminum silicate shell during the silicon oxide shell incorporation. In one embodiment, the light emitting molecules are bound to a silane molecule or functionalized with another chemical in order to promote the incorporation of the entity within the shell during fabrication. In another embodiment, the light emitting species are incorporated into the silicon oxide shell after silicon oxide shell fabrication. In another embodiment, there is another chemical step that prevents the release of the light emitting molecules after their incorporation into the silicon oxide shell. In another embodiment, other types of nanoparticles are incorporated into the silicon oxide shell during the silicon oxide growth such as magnetite, iron oxide, metal nanoparticles, metal oxide nanoparticles, gold, silver, copper, aluminum.

In an embodiment, the particles are immersed in an aqueous environment which comprises a solvent, the solution comprising at least 10%, 20%, 30%, 50%, 70%, 90%, 95% or 99% water by volume. In an embodiment, the concentration of the particles is less than 10 mg/mL, 1 mg/mL, 0.5 mg/mL, 0.2 mg/mL, 0.1 mg/mL or 0.05 mg/mL. In an embodiment, the particles are stable from dissolution in the aqueous environment. In one embodiment less than 30%, 10%, 5%, 2%, 1%, or 0.1% of the mass of the shell dissolves after 1, 2, 7, 30, or 180 days. In an embodiment, the median thickness of the shells does not change by more than 30%, 10%, 5%, 2%, 1%, or 0.1% when measured 24 hours, 2 days, 7 days, 30 days, or 180 days after immersing in the solution, compared to the median thickness prior to immersing. In some embodiments the median thickness of the particles does not change by more than 30%, 10%, 5%, 2%, 1%, or 0.1% when measured 24 hours, 2 days, 7 days, 30 days, or 180 days after immersing in a solution with a pH range between 2 and 11, 3 and 10, 4 and 9, or 5 and 9. In another embodiment, targeting ligands bound to the surface of the particle retain their targeting function for at least 1, 2, 7, 30 or 180 days.

In an embodiment, the surface of the aluminum silicate particle is functionalized with other molecules. In one embodiment, the molecules increase the stability of the silica shell in a solvent or allow the particle to be dispersed into a different solvent. Target solvents include, water, alcohols, oils, hydrocarbons, organic solvents, polar solvents, non-polar solvents, and oleophilic and oleophobic solvents. In an embodiment, the particles are functionalized with biomolecules, proteins, or DNA. In one embodiment the particles are functionalized with a linker molecule that connects molecules on the surface of the particle to another molecule that binds to the target molecule. In one embodiment the linker molecule is a heterobifunctional molecule. Examples of heterobifunctional molecules include pegylated molecules. In one embodiment the particle is incubated with a heterobifunctional linker molecule in the presence of one or more chemicals that promote the covalent attachment of the linker molecule to the surface of the particle.

In one embodiment, DNA or RNA is incorporated within an aluminum silicate shell that encapsulates a core that contains magnetic nanoparticles. In an embodiment, magnetic nanoparticles are combined with amino functionalized silane and tetraethylorthosilicate in a basic ethanol/water solution to form amino functionalized magnetic silicon oxide particles. Particles were treated with a solution of aluminum chloride solution in water and allowed to incubate for 1, 2, 5, 24 or 72 hours. The cationic magnetic silicon oxide nanoparticles were mixed with DNA and allowed to incubate for 1, 2, 5, 24 or 72 hours. Centrifugation or tangential flow filtration was used to transfer the particles into an alcohol and water mixture. Additional silane was added to the solution in the presence of base and silane to encapsulate the particles in a silicate shell. The particles were treated with a solution of aluminum chloride in water and allowed to incubate for 1, 2, 5, 24 or 72 hours. In an embodiment, the DNA magnetic nanoparticles are added to a liquid to allow their use as a tracer. To identify the type of DNA incorporated within the particle, the particles are extracted from the liquid solution using a magnet, dissolved using an etchant, and the extracted DNA is identified. In one embodiment, PCR is used to amplify the DNA to yield sufficient DNA for detection.

EXAMPLES

Example 1

Stability of Aluminum Silicate Shells Compared to Silicon Oxide Shells

Figure 8:
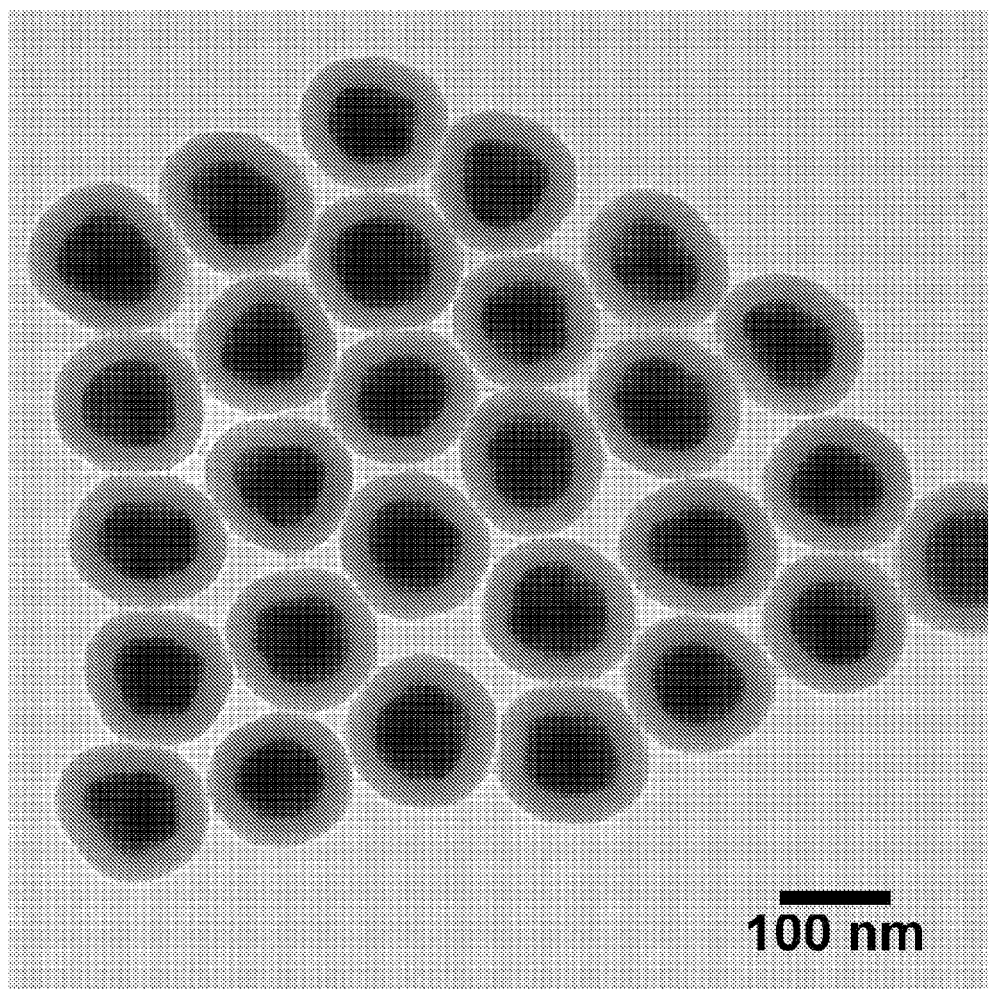
FIG. 8 is a transmission electron microscopy (TEM) image of particles having silver cores and silicon oxide shells encapsulating the cores.

In a 20 mL glass scintillation vial, 5 mL of 80 nm polyvinylpyrollidone (PVP) capped Biopure silver at a concentration of 1 mg/mL (nanoComposix, Inc.) was diluted with 10 mL of EtOH. The mixture was heated to 60° C. and 79 µL of 28% aqueous ammonium hydroxide solution was added followed by 18.3 µL of a 20 µL/mL solution of aminopropyltrimethoxysilane in ethanol. After fifteen minutes, 91.6 µL of a 20 µL/mL TEOS solution was added. The vial was capped and allowed to stir over night. Silicon oxide-shelled silver nanoparticles produced using this method are shown in FIG. 8.

250 µL of the silicon-oxide-shelled silver as synthesized was diluted to 1 mL in a microcentrifuge tube with either 0.1% 20000 MWT PEG solution or 5 mM $AlCl_3$ and allowed to incubate for 10 minutes. The PEG and $AlCl_3$ solutions were spun for 5 minutes at 10000 rpm in a microcentrifuge. The supernatant was removed and each of the solutions was diluted to 1 mL with deionized water. The centrifuge spin and redispersion in water was performed one additional time for each solution. The two solutions incubated at room temperature for 72 hours. A 2 µL aliquot of each material was dried down on a 300 mesh carbon coated formvar TEM grid and subsequently imaged. The aluminum silicate shells were intact and unchanged in thickness after 72 hours. The silicon oxide shells that were not treated with $AlCl_3$ were completed dissolved and no silicon oxide shell was visible on the TEM.

Example 2

Characterization of Aluminum Silicate-Shelled Silver Nanoparticles

Aluminum silicate-shelled silver nanoparticles were analyzed to determine the core size, shell thickness and elemental composition. FIG. 8 shows the TEM image of the particles. The contrast difference in the TEM micrograph between the silver core and the silicon oxide shell can be used to determine the diameter of the core and the thickness of the shell. ImageJ software was used to analyze the images. 100 particles were counted and the core size was determined to be 83.0±6.0 nm and the shell thickness was 26.1±2.9 nm.

The elemental composition of the different components of the particle is determined by dissolution of either the core, the shell or both and subsequent measurement by ICP-MS. The aluminum silicate coated silver particle was mixed with nitric acid which diffused through the aluminum silicate shell and dissolved the silver. The silver ions were isolated from the aluminum silicate by centrifugation and measured by ICP-MS. To quantify the amount of silicon oxide and aluminum present in the shells, the aluminum silicate was dissolved in HF. The dissolved silicon and aluminum species were analyzed. The ratio of the aluminum to silicon atoms was determined to be 1.5:100.

Example 3

Stability of Aluminum Silicate Shells Compared to Thermally Condensed Silicon Oxide Shells The effect of thermal treatments and aluminum treatments on silicon oxide was compared. In a 20 mL glass scintillation vial, 5 mL of 80 nm polyvinylpyrollidone (PVP) capped Biopure gold at a concentration of 1 mg/mL (nanoComposix, Inc.) was diluted with 10 mL of EtOH. The mixture was heated to 60° C. and 79 µL of 28% aqueous ammonium hydroxide solution was added followed by 18.3 µL of a 20 µL/mL solution of aminopropyltrimethoxysilane in ethanol. The solution was heated for 10 hours at 60° C. in a sealed scintillation vial. TEM analysis showed a silicon oxide shell on the gold nanoparticles after the heating step. 333 µL of the heat treated material was diluted to 1 mL with DI water, spun out at 4400 rpm in a microcentrifuge tube and resuspended in water. The supernatant was decanted, the pelleted material taken back up in 1 mL water and centrifuged again. This was then repeated a third time. The final 1 mL sample was heated to 90° C. in a capped 4 mL glass vial for 30 minutes, and examined by TEM. No silicon oxide shell was observed on the surface of the gold nanoparticles.

In parallel, a 333 µL aliquot of the silicon oxide coated gold nanoparticles in ethanol was diluted to 1 mL with 5 mM AlCl3, incubated for 30 minutes and then washed three times into water. This sample was heated to 90° C. on a hotplate for 30 minutes and then analyzed by TEM. The silicon oxide shells were unchanged from their initial analysis in ethanol.

Example 4

Aluminum Silicate-Shelled Silver Nanoparticle-Quantum Dot Composite Particles 11.2 mg of 100 nm silver nanoparticles coated with a 20 nm silicon oxide shell was diluted in 1.6 mL of water and 3.2 mL of isopropanol. 485 µL of 30% NH4OH and 15.4 µL of a 20 µL/mL solution of aminopropyltriethoxysilane in isopropanol was added to the silicon oxide-shelled silver reaction solution and stirred for 15 min. 1.2 mL of a 20 µL/mL solution of tetraethoxysilane in isopropanol was added to the scintillation vial and stirring was continued overnight. The solution was diluted to twice its total volume with 5 mM $AlCl_3$, incubated for 5 minutes and then centrifuge washed 3× into a 10 mM pH 8 phosphate buffer at pH 8 with 1 mg/mL 20K MWT PEG at 2,900 RCF in a microcentrifuge tube. Another solution was prepared that did not incubate the particles with $AlCl_3$. Quantum dots (Life Technologies) with a peak emission resonance of ~800 nm were surface functionalized with lipoic acid and incubated with the aluminum silicate-shelled silver particles. The particles were centrifuged at 2,900 RCF to separate free quantum dots from dots attached to the aluminum silicate-shelled silicon oxide-shelled silver surface. The particles were treated with N-succinimidyl-4-formylbenzamide heterobifunctional cross linker (Solulink) and incubated with 0.1 mg of 6-hydrazinonicotinamide (Solulink) treated streptavidin, both prepared following Solulink's binding protocols. The streptavidin particles were added to the sample pad of a lateral flow strip that has a capture line of biotinylated BSA. The quantum dot coated silicon oxide particles that were treated with $AlCl_3$ strongly bound to a lateral flow assay test strip after storage times >1 month. The particles that were not treated with $AlCl_3$ had <20% of the binding signal to the capture line compared to the signal of the $AlCl_3$ treated particles of the lateral flow strips after 1 week of storage.

Example 5

Encapsulated DNA in Magnetic Aluminum Silicate Nanoparticles

Magnetite nanoparticles isolated from magnetic ink printer cartridges were treated with a mixture of aminopropyltrimethoxysilane and tetraethylorthosilicate under base hydrolysis conditions in alcohol. 2 mL of a 22.3 mg/mL solution of polyvinylpyrrolidone capped magnetite particles were prepared at 1 mg/mL in a 3:1 ethanol:water solution. To this solution, 0.22 mL of a 30% $NH_4OH$ solution (Sigma Aldrich) was added. After 5 minutes of magnetic stirring, a total of 0.79 mL of a freshly prepared solution of 66 µL of tetraethylorthosilicate, 20 µL of 1:20 aminopropyltrimethoxysilane in ethanol, and 700 µL of ethanol was added and the solution was allowed to stir overnight. After isolation of the particles from the alcoholic base solution by centrifugation and water wash, the magnetic nanoparticles that are encapsulated by silicon oxide were treated with a solution of $AlCl_3$ in water (5 mM) for 1 h followed by isolation and washing by centrifugation. The zeta potential of the aluminum chloride treated particles was +45 mV at pH 7.

1 mL of the cationic magnetic silicon oxide particles was diluted to 6.5 mL with water. 200 µL of 0.459 µg/mL of bacterially derived plasmid DNA was added. The suspension was incubated overnight at room temperature. Excess DNA was removed from the particles via centrifugation. A reduced zeta potential (+20 mV) indicates that DNA binding has occurred. An encapsulating aluminum silicate shell is grown to help protect the bound DNA from high temperatures and chemical reaction. The aqueous particle solution is treated with aminopropyltrimethoxysilane and tetraethylorthosilicate in water. The particles are mixed with 2.5 mL of water and 5 mL of ethanol. 6.8 µL of freshly prepared aminopropyltrimethoxysilane at 50 µL/mL in ethanol is added. After ten minutes, 680 µL of freshly prepared tetraethylorthosilicate at 50 µL/mL in ethanol is added. The solution is incubated for 48 hours.

The magnetic DNA nanoparticles are isolated with a magnet and rinsed from reaction byproducts. Half of the particles were incubated in a 5 mM solution of $AlCl_3$ for 3 h before again isolating via magnet and washing with water. After heating, both the $AlCl_3$ and untreated magnetic DNA nanoparticles to 90° C. for 24 hours, the DNA was recovered from the particles by treatment of the particles with an ammonium buffered HF solution followed by isolation on a Qiagen DNA concentration spin column. The particles are isolated using centrifugation or on a magnet and are soaked in an aqueous solution of $NH_4F.HF$ and $NH_4F$ (150 µL of 1 M solution of each) for ten minutes with bath sonication. DNA was isolated with a QIAquick PCR purification kit from Qiagen utilizing the materials and instructions contained therein. Subsequent qPCR of the DNA demonstrated that >40% of the DNA could be recovered for the $AlCl_3$ treated particles while <10% of the DNA could be recovered from the particles that were not treated with $AlCl_3$.

Example 6

Aluminum Silicate Stabilization of Silver Nanoplates

Silver nanoplates have a rapid dissolution rate when placed in water. The dissolution rate is reduced when the silver nanoplates are-shelled with aluminum silicate. In this example, the stability of aluminum silicate shells is compared to that of silver nanoplates with a silicon oxide shell that is not aluminum chloride treated.

Figure 9:
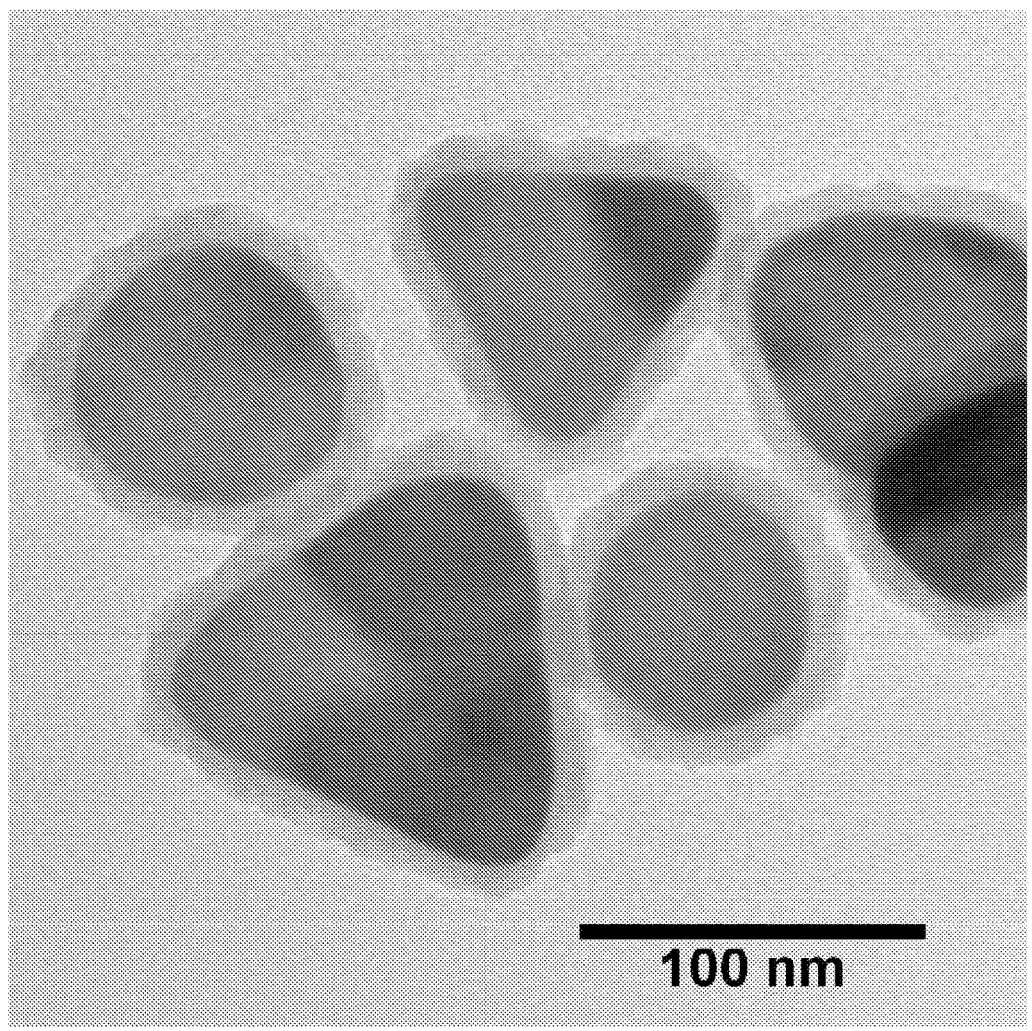
FIG. 9 is a TEM image of particles having silver cores encapsulated with silicon oxide shells, taken after encapsulating.
Figure 10:
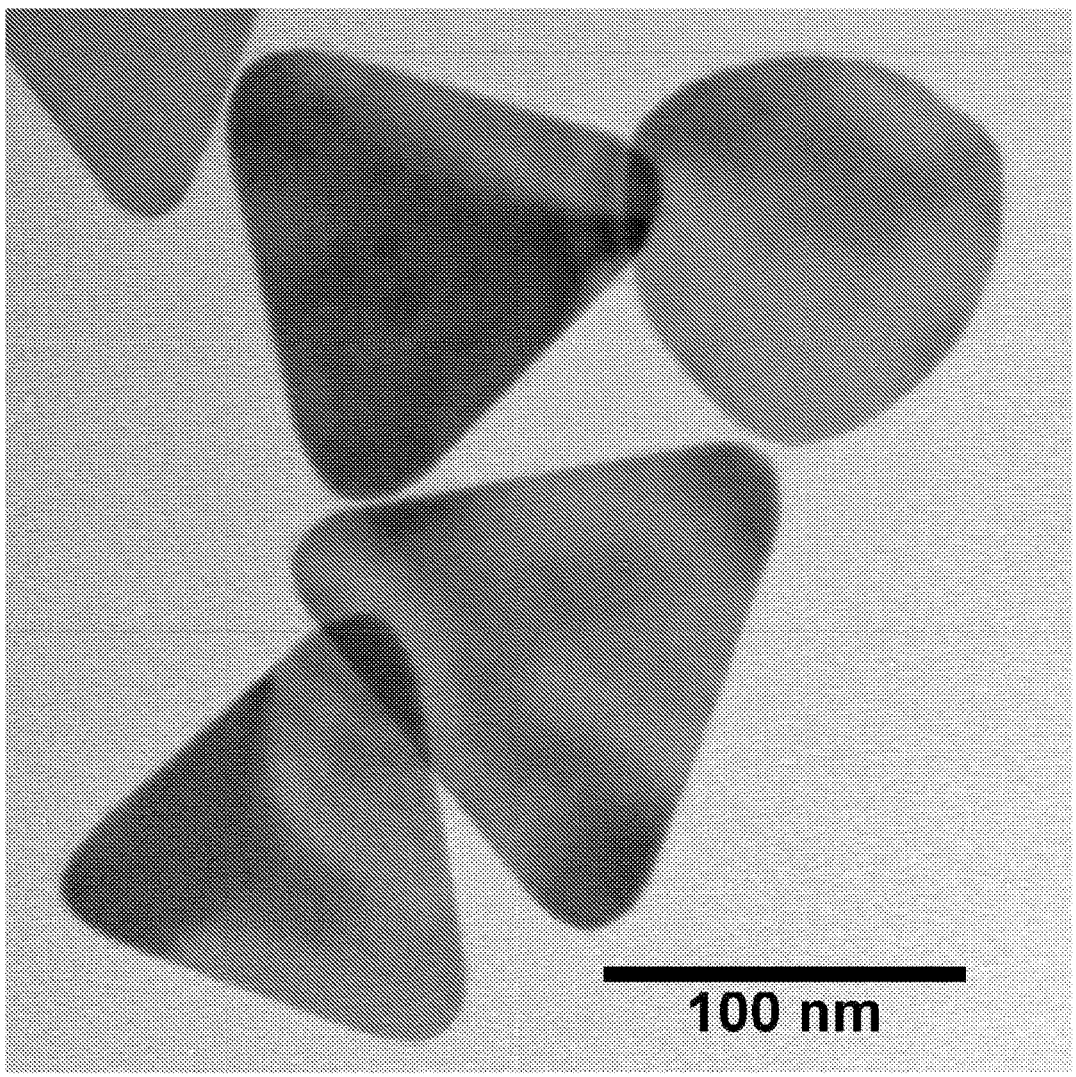
FIG. 10 is a TEM image of particles having silver cores encapsulated with silicon oxide shells, taken after encapsulating and immersing in water for 24 hours after encapsulating.
Figure 11:
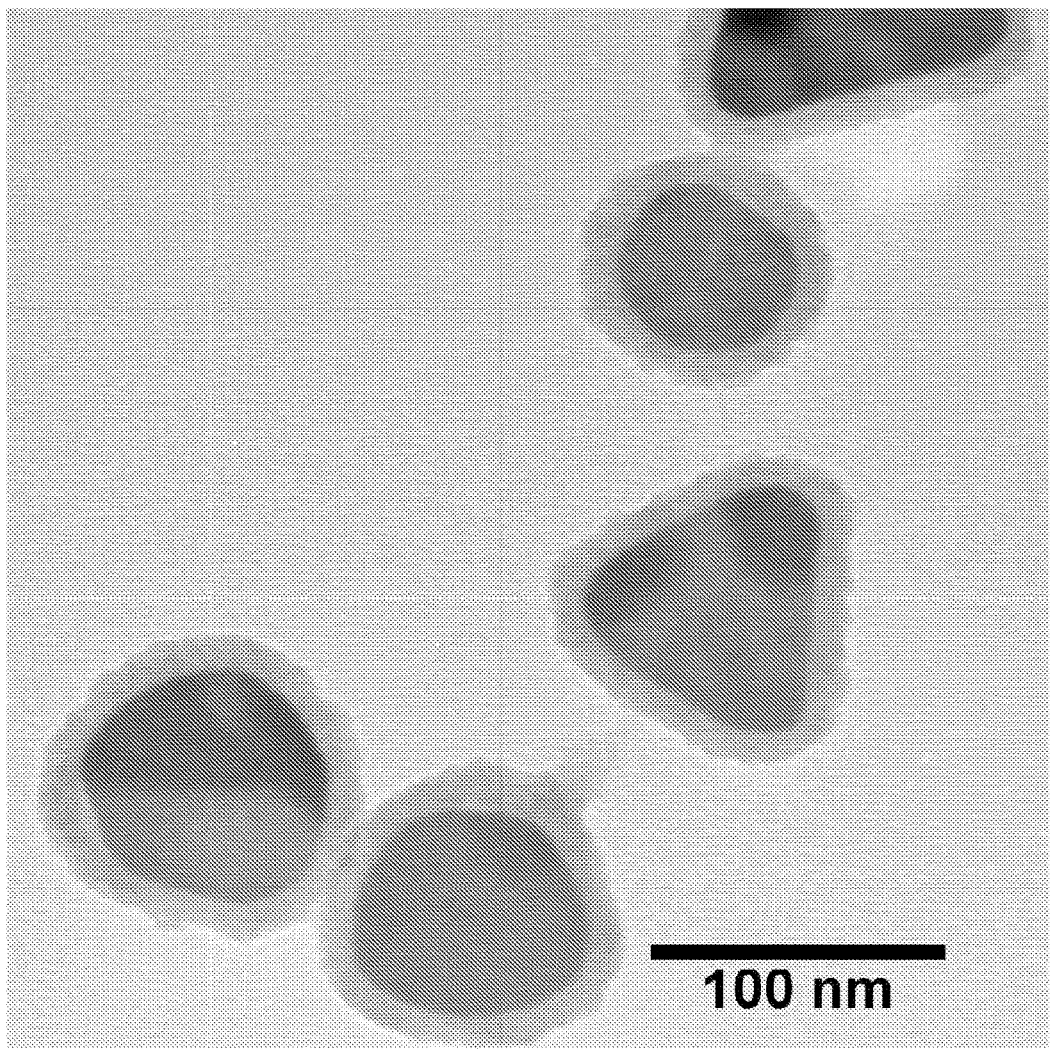
FIG. 11 is a TEM images of particles having silver cores encapsulated with silicon oxide shells having aluminum incorporated therein, taken after encapsulating and immersing in water for 20 days after encapsulating.
Figure 12:
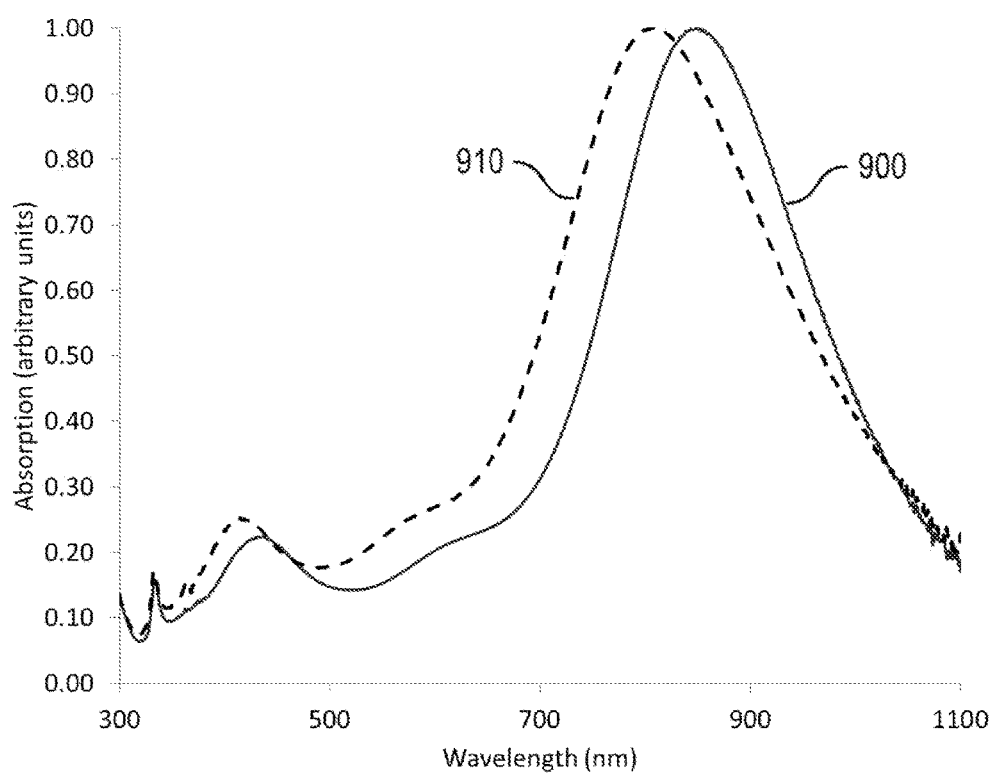
FIG. 12 show optical absorbance spectra of particles having silver cores and silicon oxide shells, taken after encapsulating the cores with the shells, and after immersing in water for 24 hours after encapsulating.
Figure 13:
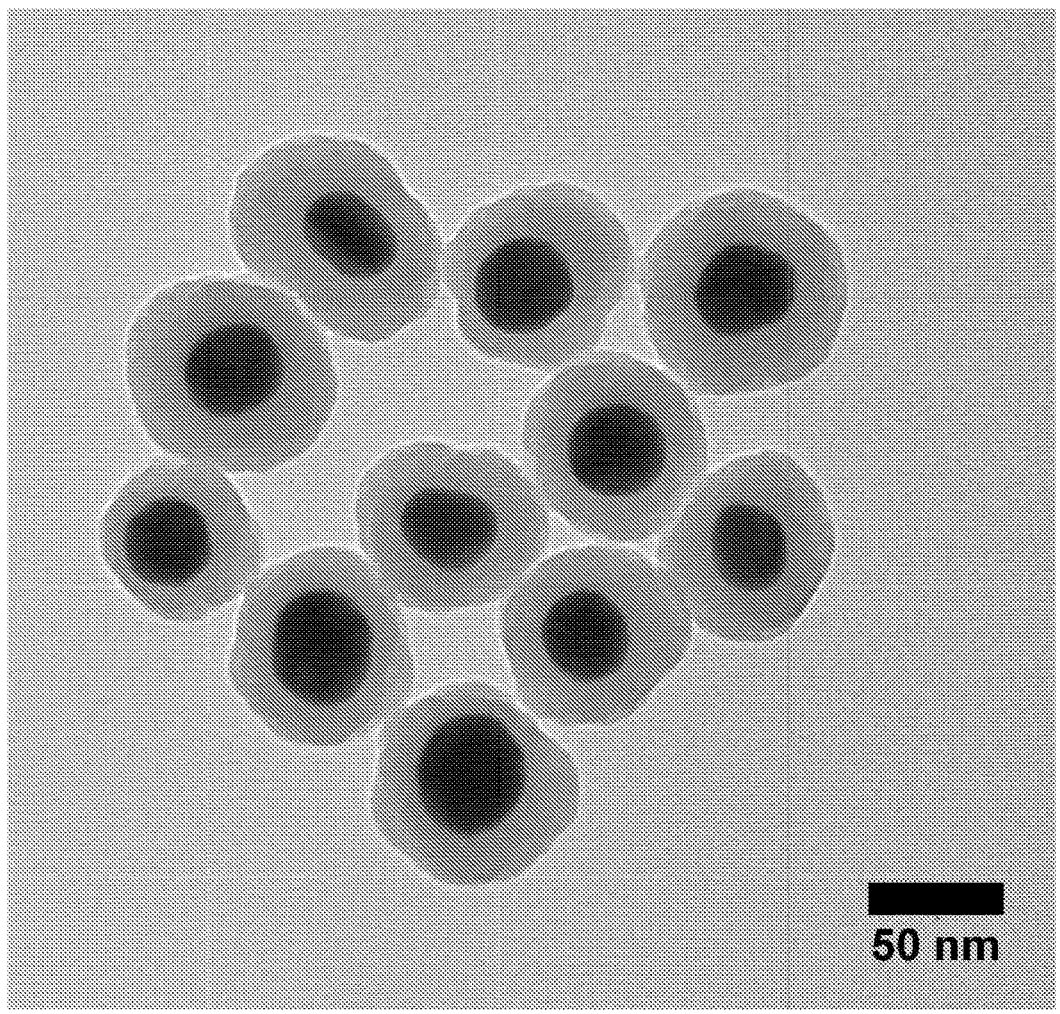
FIG. 13 is a TEM image of particles having silver cores encapsulated with silicon oxide shells having aluminum incorporated therein, according to some embodiments.

A silicon oxide shell was grown on the surface of 800 nm resonant (~75 nm diameter polyvinylpyrrolidone (PVP) capped silver nanoplates). 600 mL of a solution of 800 nm resonant PVP capped silver nanoplates at a concentration of 1 mg/mL was added to 3.5 L of reagent grade ethanol and 270 mL Milli-Q water under constant stirring. 4.3 mL of dilute aminopropyltriethoxysilane (215 µL APTES in 4.085 mL isopropanol) was then added to the solution, followed immediately by the addition of 44 mL of 30% ammonium hydroxide. After 15 minutes of incubation, 31 mL of dilute tetraethylorthosilicate (1.55 mL TEOS in 29.45 mL isopropanol) was added to the solution. The solution was then left to stir overnight. A transmission electron microscopy image of the silicon oxide-coated nanoplates is shown in FIG. 9. A 10 nm thick silicon oxide shell is formed. Half of the silicon oxide-shelled nanoplate solution was incubated with 5 mM $AlCl_3$ for 30 minutes. Both the aluminum silicate-shelled plates and the silicon oxide-shelled plates were washed with centrifugation 3× into water. After one day, the silicon oxide-shelled plates were imaged with TEM and the silicon oxide shell had completely dissolved as is shown in FIG. 10. After twenty days, the thickness of the aluminum silicate-shelled plates had not changed (FIG. 11). The dissolution of the silicon oxide shell impacts the optical stability of the nanoplates. An optical spectrum of the silicon oxide nanoplates initially 900 and after 24 hours 910 is shown in FIG. 12. The peak optical resonance of the nanoplates coated with silicon oxide shifted by 40 nm during the 24 hours. There was no change to the optical resonance peak of the aluminum silicate-shelled plates.

Example 7

Coating of Clusters of Magnetic Nanoparticles

Clusters of magnetic nanoparticles were prepared as described in "Assembly of Magnetically Tunable Photonic Crystals in Nonpolar Solvents", JACS Communications, 131, 3484-3486, 2009. Clusters of magnetic nanoparticles were coated with silicon oxide by adding 0.5 mL of $NH_4OH$ and 10 mL of ethanol to 1.5 mL of coated clusters of magnetic nanoparticles. 75 µL of TEOS was added and the material was shaken at 600 RPM on a vortexer for 1 hour. After 1 hour, a second injection of 75 µL TEOS was added to the solution and vortexed for 1 hour. The sample was split into two equal aliquots. One aliquot was treated with 1 mL of 25 mM $AlCl_3$ for 10 minutes. Both samples were separated with a magnet and washed with water. 100 µL of the aluminum silicate-shelled magnetic nanoparticles was added to 10 mL of solution and allowed to incubate at 30° C. for 72 hours. A 100 µL aliquot of untreated silicon oxide magnetic nanoparticles was also incubated under the same conditions. TEM analysis of the magnetic nanoparticles after 72 hours shows that the non-AlCl₃ treated silicon oxide shell has partially dissolved and an increase in the shell porosity is observed for the sample that was not exposed to aluminum chloride. There was no change to the AlCl₃ silicon oxide shell over the 72 hour period.

Example 8

Bioconjugation of Aluminum Silicate Surface Enhanced Fluorescent Nanoprobes 150 nm gold nanoshells were silicon oxide-shelled with a 15 nm silicon oxide shell made using aminopropyltriethoxy silane and IRDye 800CW NHS ester (Licor). 1 mL of a 3 OD gold nanoshell solution was spun in a microcentrifuge tube and resuspended in 5 mM AlCl₃ for 15 minutes. The solution was washed 3 additional times into a pH 6 buffer consisting of 100 mM PBS and 150 mM NaCl. HyNic (Solulink) was added to the particles and 4FB (Solulink) to the streptavidin. The materials were combined and put on a rotator for 4 hours. 30 µL of the surface enhanced dyes were added to a lateral flow strip and their binding efficacy was evaluated. The aluminum silicate-shelled gold nanoshells showed consistent binding to a biotinylated signal stripe after storage in aqueous buffers for greater than 30 days.

Example 9

Aluminum Silicate Shell on Clusters of Magnetic Nanoparticles

Highly water-soluble magnetite nanocrystals with average size of 11.5 nm were synthesized in solution at high temperature following the procedure outlined in (J. Ge, L. He, J. Goebl, and Y. Yin, "Assembly of Magnetically Tunable Photonic Crystals in Nonpolar Solvents, (2009) JACS, 131 (10), 3484). A mixture of 4 mM of poly(acrylic acid), 2 mM of FeCl₃, and 15 mL of diethylene glycol (DEG) was heated to 220° C. in a nitrogen atmosphere with vigorous stirring. 4 mL of NaOH/DEG stock solution (2.5 mol/L) was then injected into the above solution which turned black immediately. After the temperature reached 220° C. again, another 5 mL of FeCl₃ stock solution (0.4 mol/L) was added into the reaction mixture. Another 3 mL of NaOH/DEG stock solution (2.5 mol/L) was then injected at 220° C. The resulting mixture was further heated for 10 min to yield 11.5 nm Fe₃O₄ nanocrystals. These colloids were first washed with a mixture of deionized (DI) water and ethanol several times to remove additional surfactant and salt, and finally dispersed in 1 mL of DI water. The volume fraction of Fe₃O₄ in the final ferrofluid was about 5%. 0.5 mL of the ferrofluid was diluted to 3 mL and was mixed with ethanol (20 mL), aqueous ammonia (28%, 1 mL) under vigorous magnetic stirring. Tetraethylorthosilicate (0.2 mL) was injected to the solution, and the mixture was allowed to react for 40 min. The silicon oxide-shelled Fe₃O₄ clusters were centrifuged and resuspended in a 5 mM solution of AlCl₃ for 15 minutes. The aluminum silicate coated Fe₃O₄ nanoclusters were centrifuged and suspended in water. The magnetically induced optical properties of the aluminum chloride treated particles remained stable for 20 days in water while the untreated particles had a degraded optical signature.

Example 10

Fabrication of Hollow Aluminum Silicate Particles

The preparation of small porous hollow nanoparticles is of interest for the delivery of drugs. Hollow silicon oxide nanoparticles are prepared via a template method. Silicon oxide shells are grown on the surface of gold nanoparticles and the gold nanoparticles are subsequently dissolved through the use of a cyanide solution, leaving behind a hollow porous silicon oxide shell. In a 20 mL scintillation vial, 4 mL of a 0.89 mg/mL aqueous solution of 33 nm PVP capped gold nanoparticles was dissolved in 10.8 mL of anhydrous ethanol. 17.3 µL of APTES at 50 µL/mL in ethanol and 136 µL of 30% w/v ammonium hydroxide solution were added. The solution was stirred for 15 minutes at room temperature followed by the addition of 86.3 µL of TEOS at 50 µL/mL.

A portion of the particles are incubated in 10 mM AlCl₃ for 3 hours. 3 additional centrifuge and wash cycles are performed on both AlCl₃ treated and untreated silicon oxide-coated gold nanoparticles. Untreated silicon oxide shells are dissolved after the centrifuge washes. The treated shells remain unchanged.

Example 11

Figure 14:
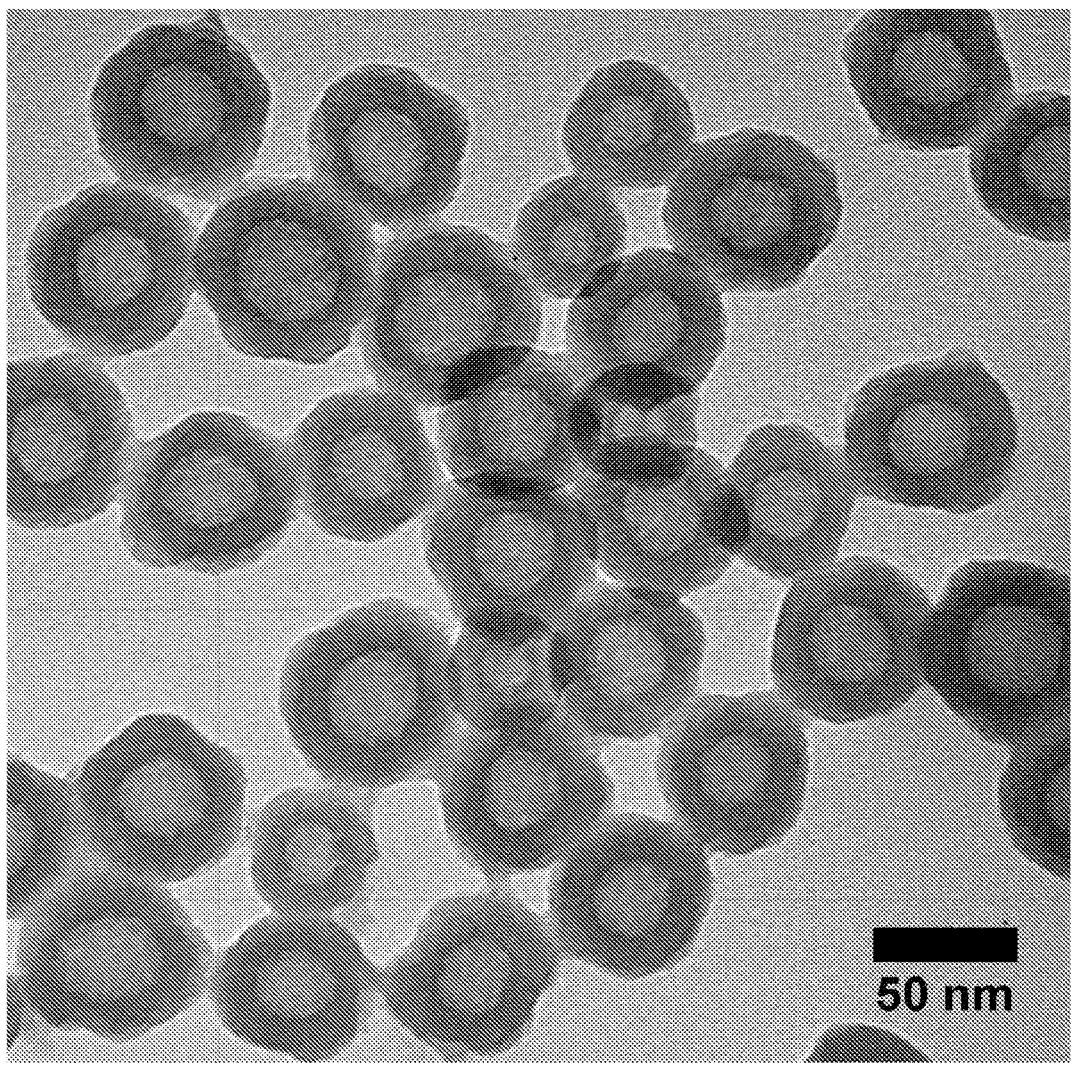
FIG. 14 is a TEM image of particles having hollow cavities therein.

Dissolution of the Gold Cores from Silicon Oxide-Shelled Nanoparticles to Leave Hollow Silicon Oxide Particles 10 mL of gold coated silicon oxide particles was incubated with 10 mM AlCl₃ for 1 hour. 600 µL of a 0.5 M solution of sodium cyanide was added. The solution was incubated for 24 h and the suspension pelleted in a centrifuge followed by washing with deionized water. The change in color from red to clear indicates that the gold core is dissolved. An image of the hollow aluminum silicate shells is shown in FIG. 14. If no AlCl₃ is added, stable hollow silicon oxide shells are not formed.

Hollow aluminum silicate shells were surface functionalized with a heterobifunctional cross linker via surface amines. A cross-linker with an NHS ester at one end for amide reactivity and a maleimide linker at the other end for thiol reactivity was used to bind reduced HER2 targeting FAB' fragments to the surface of the hollow silicon oxide nanoparticles. The particles were subsequently loaded with doxorubicin by soaking in a concentrated solution of doxorubicin in water leading to a 15% by mass loading of doxorubicin relative to the mass of the silica. The doxorubicin was released with a half-life of approximately 15 h when the particles were washed into a doxorubicin free buffer.

The foregoing description details certain embodiments of the invention. It will be appreciated, however, that no matter how detailed the foregoing appears in text, the invention may be practiced in many ways. It should be noted that the use of particular terminology when describing certain features or aspects of the disclosure should not be taken to imply that the terminology is being re-defined herein to be restricted to including any specific characteristics of the features or aspects of the disclosure with which that terminology is associated.

What is claimed is:
1. A material composition, comprising:
   a plurality of particles, wherein each particle comprises a core and a shell encapsulating the core, the shell comprising at least one atomic element not included in the core,
   wherein the cores have:
      a median maximum dimension that is less than 10 microns, and a median of at least one axial dimension that is in the range of 10 nm to 500 nm, and
wherein the shells have:
a median thickness that is less than 100 nm,
a silicon concentration that is in the range of 10% to 50% on the basis of the weight of the shells, and
an aluminum concentration that is in the range of 0.01% to 5% on the basis of the weight of the shells, wherein the shells have a ratio of the aluminum concentration to the silicon concentration in the range of 1:20 to 1:5000 such that the median thickness does not change by more than 10% when measured 24 hours after immersing in water.

2. The material composition of claim 1, wherein the shells comprise a three-dimensional network of interconnected molecular units, comprising:
a first plurality of molecular units having a chemical formula $SiO_x(OH)_y$, wherein $x+y \leq 4$ and $x$ is $\geq 1$;
a second plurality of molecular units having a chemical formula $SiO_a(OH)_b R_c$, wherein $a+b+c \leq 4$, a is $\geq 1$ and R is a chemical group having a carbon atom that is directly bonded to a silicon atom; and
a third plurality of molecular units having a chemical formula $AlO_m(OH)_n$, wherein $m+n \leq 6$ and m is $\geq 1$,
wherein at least one oxygen atom in each of the first, second and third molecular units is covalently bonded to two silicon atoms, to a silicon atom and an aluminum atom, or to two aluminum atoms.

3. The material composition of claim 2, wherein R comprises a chemical group selected from the group consisting of an amine, a thiol, a carboxylic acid, an azide, an aldehyde, an epoxide and combinations thereof.

4. The material composition of claim 1, wherein at least 95% of the shells, on the basis of atomic percentage, comprise silicon, carbon, oxygen, hydrogen, and aluminum.

5. The material composition of claim 4, wherein at least 98% of the shells further comprise nitrogen and sulfur.

6. The material composition of claim 1, further comprising a liquid in which the particles are immersed, the liquid comprising at least 50% water by volume.

7. The material composition of claim 1, wherein the core has a shape selected from the group consisting of a sphere, a spheroid, an ellipsoid, a pyramid, a prism, a cube, a plate, a disc, a rod and a hollow sphere.

8. The material composition of claim 1, wherein the core comprises an element selected from the group consisting of gold, silver, platinum, palladium, copper, aluminum, nickel, and iron.

9. The material composition of claim 1, wherein the core comprises an inorganic oxide.

10. The material composition of claim 9, wherein the core includes an inorganic oxide selected from the group consisting of $SiO_2$, $TiO_2$, $Fe_2O_3$, $Fe_3O_4$, CuO, $Cu_2O$, ZnO, $Y_2O_3$, $ZrO_2$, $Nb_2O_5$, $MoO_3$, $In_2O_3$, $SnO_2$, $Sb_2O_5$, $Ta_2O_5$, $WO_3$, PbO and $Bi_2O_3$, and combinations thereof.

11. The material composition of claim 1, wherein at least one of the core and the shell comprises a plurality of nanoparticles incorporated therein, wherein the nanoparticles have a median maximum dimension that is less than 100 nm.

12. The material composition of claim 11, wherein the nanoparticles are selected from the group consisting of quantum dot nanoparticles, magnetic nanoparticles, up-converting nanoparticles, down-converting nanoparticles, gold nanoparticles, silver nanoparticles, aluminum nanoparticles, copper nanoparticles and combinations thereof.

13. The material composition of claim 12, wherein the nanoparticles are quantum dot nanoparticles comprising a semiconductor material selected from the group consisting of Si, Ge, CdS, CdSe, CdTe, ZnS, ZnSe, ZnTe, GaAs, GaP, GaAs, GaSb, HgS, HgSe, HgTe, InAs, InP, InSb, AlAs, AlP, and AlSb, wherein the quantum dot nanoparticles emit light having a peak wavelength at least 10 nanometers shorter than an emission wavelength of a bulk semiconductor material having the same composition as the semiconductor material.

14. The material composition of claim 11, wherein the nanoparticles have a core-shell structure, wherein the nanoparticles have a nanoparticle core comprising the semiconductor material and a nanoparticle shell comprising a material different from the nanoparticle core material.

15. The material composition of claim 11, wherein the nanoparticles are magnetic nanoparticles selected from the group consisting of iron, cobalt, nickel, gadolinium, dysprosium iron and their associated oxides, wherein the nanoparticles have a magnetic moment that is at least 1 emu/g.

16. The material composition of claim 11, wherein at least 90% of the nanoparticles have a median edge-to-edge spacing of at least 2 nm.

17. The material composition of claim 11, wherein at least 90% of the nanoparticles have a median edge-to-edge spacing of less than 2 nm.

18. The material composition of claim 1, wherein each particle further comprises a plurality of nanoparticles formed at an interface between the core and the shell, wherein the nanoparticles are in contact with the core but formed outside of the core.

19. The material composition of claim 1, wherein each particle further comprises a plurality of nanoparticles formed at surfaces of the shells.

20. The material composition of claim 18, wherein each particle further comprises an intermediate shell interposed between the core and the shell, wherein the intermediate shell comprises a material different than the core and the shell.

21. The material composition of claim 20, wherein one or both of the shell and the intermediate shell comprises a metal or an inorganic metal oxide.

22. The material composition of claim 20, wherein at least one of the core, the intermediate shell and the shell comprises a plurality of nanoparticles incorporated therein, wherein the nanoparticles have a median maximum dimension that is less than 100 nm.

23. The material composition of claim 20, wherein each particle further comprises a plurality of nanoparticles formed at one or both of an interface between the core and the intermediate shell and an interface between the intermediate shell and the shell.

24. The material composition of claim 1, further comprising a bifunctional linker molecule or a biomolecule attached to a surface of each particle.

25. The material composition of claim 1, further comprising a molecule selected from the group consisting of a protein, antibody, DNA, RNA and combinations thereof, wherein the molecule is bonded to a particle surface.

26. The material composition of claim 1, wherein the particles further comprise a molecule selected from the group consisting of a protein, antibody, DNA, RNA and a combination thereof, wherein the molecule is encapsulated within the core and/or the shell.

27. The material composition of claim 1, further comprising a molecule selected from the group consisting of a sugar, a small organic molecule, a polymer molecule and a combination thereof, wherein the molecule is attached to a particle surface.

28. The material composition of claim 1, wherein a surface of each particle is functionalized with a functional group selected from the group consisting of a thiol group, a carboxyl group, an aldehyde group, a carboxylic acid group, hydrazide group, an amine group and combinations thereof.

29. The material composition of claim 1, wherein at least one of the core or the shell includes a light-emitting center incorporated therein, wherein the light-emitting center is selected from the group consisting of fluorophore, dye, luminophore, a chemiluminescent species and phosphor.

30. The material composition of claim 1, further comprising one or more light-emitting centers attached to a surface of each of the particles.

31. The material composition of claim 1, further comprising a plurality of quantum-dot nanoparticles attached to a surface of each of the particles, wherein the quantum-dot nanoparticles are functionalized with a molecule selected from the group consisting of protein, antibody, DNA, RNA and a combination thereof.

32. The material composition of claim 1, wherein the core comprises a silicon oxide having a plurality of magnetic nanoparticles incorporated therein, and wherein the shell comprises a DNA molecule, an RNA molecule and/or a peptide molecule.

33. A method of preparing a material composition, comprising:
providing a plurality of particle cores;
encapsulating the particle cores with shells comprising at least one atomic element not included in the cores; and
incorporating aluminum into the shells by exposing the shells to an aluminum-containing material to thereby provide a plurality of particles,
wherein the particle cores have:
a median maximum dimension that is less than 10 microns, and
a median of at least one axial dimension that is in the range of 10 nm to 500 nm, and
wherein the shells have:
a median thickness that is less than 100 nm,
a silicon concentration that is in the range of 10% to 50% on the basis of the weight of the shells, and
an aluminum concentration that is in the range of 0.01% to 5% on the basis of the weight of the shells,
wherein the shells have a ratio of the aluminum concentration to the silicon concentration in the range of 1:20 to 1:5000 such that the median thickness does not change by more than 10% when measured 24 hours after immersing in water.

34. The method of claim 33, further comprising immersing the particles in a liquid that comprises at least 50% water by volume.

35. The method of claim 34, wherein the shells do not substantially dissolve in the liquid such that the median thickness of the shells does not reduce by more than 2 inn in the liquid at room temperature.

36. The method of claim 34, further comprising storing the immersed particles in the liquid for at least 24 hours, wherein the median thickness of the shells does not change by more than 10% when measured 24 hours after immersing in the liquid, compared to the median thickness prior to immersing.

37. The method of claim 33,
wherein encapsulating the particle cores comprises forming a three-dimensional network of interconnected molecular units surrounding the particle cores, wherein the three-dimensional network comprises:
a first plurality of molecular units having a chemical formula $SiO_x(OH)_y$, wherein $x+y \leq 4$ and x is $\geq 1$, and
a second plurality of molecular units having a chemical formula $SiO_a(OH)_b R_c$, wherein $a+b+c \leq 4$, a is $\geq 1$ and R is a chemical group having a carbon atom that is directly bonded to a silicon atom; and
wherein incorporating aluminum into the shells comprises incorporating aluminum into the three-dimensional network such that the three dimensional network is modified to include a third plurality of molecular units having a chemical formula $AlO_m(OH)_n$, wherein $m+n \leq 6$ and m is $\geq 1$, and
wherein at least one oxygen atom in each of the first, second and third molecular units is covalently bonded to two silicon atoms, to a silicon atom and an aluminum atom, or to two aluminum atoms.

38. The method of claim 33, wherein encapsulating the cores comprises forming a silicon oxide via a condensation reaction in a solution containing at least one silane having a chemical formula given by $X_n SiY_{(4-n)}$,
wherein $0<n<4$, and
wherein one or both of X and Y is each independently selected from the group consisting of OEt, OMe, Cl, Br, I, H, alkyl, fluoroalkyl, perfluoroalkyl, alkoxide, aryl, alkyl amine, alkyl thiol and combinations thereof.

39. The method of claim 38, wherein the at least one silane is selected from the group consisting of aminopropyltriethoxy silane, aminopropyltrimethoxy silane, mercaptopropyltriethoxysilane, mercaptopropylmethoxysilane, tetramethoxy silane, tetraethoxy silane, and combinations thereof.

40. The method of claim 33, wherein incorporating aluminum comprises exposing the shells to a solution having an aluminum salt dissolved therein.

41. The method of claim 40, wherein the aluminum salt is aluminum chloride.

42. The method of claim 40, wherein the concentration of the aluminum salt in the solution is in the range of 0.1 mM to 100 mM.

43. The method of claim 40, wherein incorporating aluminum is performed during encapsulating the cores by adding the aluminum salt to the solution while the particle cores are being encapsulated with the shells.

44. The method of claim 40, wherein incorporating aluminum is performed after encapsulating the cores by transferring cores encapsulated with the shells to an aqueous solvent before the aluminum salt is dissolved therein.

45. The method of claim 40, wherein the solution has a pH having a range selected from the group consisting of 1 to 3, 2 to 4, 3 to 5, 4 to 6, 5 to 7, 6 to 8 and 7 to 9.

46. The method of claim 33, wherein the provided plurality of particle cores comprises an element selected from the group consisting of silver, gold, aluminum and copper.

47. The method of claim 33, wherein the provided plurality of particle cores comprise an inorganic oxide selected from the group consisting of $SiO_2$, $TiO_2$, $Fe_2O_3$, $Fe_3O_4$, CuO, $Cu_2O$, ZnO, $Y_2O_3$, $ZrO_2$, $Nb_2O_5$, $MoO_3$, $In_2O_3$, $SnO_2$, $Sb_2O_5$, $Ta_2O_5$, $WO_3$, PbO and $Bi_2O_3$, and combination thereof.

48. The method of claim 33, further comprising incorporating a plurality of nanoparticles into at least one of the cores and the shells, wherein the nanoparticles have a median maximum dimension that is less than 100 nm.

49. The method of claim 33, further comprising forming a plurality of nanoparticles at one or both of interfaces between the cores and the shells and surfaces of the particles.

* * * * *

UNITED STATES PATENT AND TRADEMARK OFFICE
CERTIFICATE OF CORRECTION

PATENT NO. : 9,675,953 B2
APPLICATION NO. : 15/027426
DATED : June 13, 2017
INVENTOR(S) : Steven J. Oldenburg et al.

It is certified that error appears in the above-identified patent and that said Letters Patent is hereby corrected as shown below:

In the Specification

In Column 10 at Line 28, Change "dimethoxysi lane," to --dimethoxysilane,--.

In Column 15 at Line 63, Change "dimethoxyfluoresce in," to --dimethoxyfluorescein,--.

In Column 22 at Line 3, Change "polyvinylpyrollidone," to --polyvinylpyrrolidone,--.

In Column 22 at Lines 3-4, Change "cetyl trimethylammonium bromide," to --cetyltrimethylammonium bromide,--.

In Column 22 at Line 14, Change "mercaptoproprionic" to --mercaptopropionic--.

In Column 22 at Line 15, Change "polyvinylpyrollidone," to --polyvinylpyrrolidone,--.

In Column 22 at Line 39, Change "silasanes." to --silazanes.--.

In Column 22 at Line 49, After "silane," delete "aminopropyltrimethoxy silane,".

In Column 25 at Line 19, Change "polyvinylpyrollidone" to --polyvinylpyrrolidone--.

In Column 26 at Line 14, Change "polyvinylpyrollidone" to --polyvinylpyrrolidone--.

In the Claims

In Column 32 at Line 36, In Claim 20, change "claim 18," to --claim 1,--.

In Column 33 at Line 57, In Claim 35, change "inn" to --nm--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*